(12) United States Patent
Deng et al.

(10) Patent No.: US 11,602,514 B2
(45) Date of Patent: Mar. 14, 2023

(54) MEDICAMENT HAVING ANTI-INFLAMMATORY BOWEL DISEASE FUNCTION, AND PREPARATION METHOD THEREFOR AND APPLICATION THEREOF

(71) Applicant: SUZHOU PHARMAVAN CO., LTD, Jiangsu (CN)

(72) Inventors: Shiping Deng, Suzhou (CN); Yu Cao, Suzhou (CN); Zhi Li, Suzhou (CN); Yunhui Yu, Suzhou (CN); Kui Zhang, Suzhou (CN); Minjie Zhang, Suzhou (CN); Gaogang Yuan, Suzhou (CN); Tao Xu, Jiangsu (CN); Gang Yu, Suzhou (CN); Chuanliang Jiang, Suzhou (CN)

(73) Assignee: SUZHOU PHARMAVAN CO., LTD, Jiangsu (CN)

( * ) Notice: Subject to any disclaimer, the term of this patent is extended or adjusted under 35 U.S.C. 154(b) by 0 days.

(21) Appl. No.: 17/043,428

(22) PCT Filed: Jul. 28, 2018

(86) PCT No.: PCT/CN2018/097685
§ 371 (c)(1),
(2) Date: Sep. 29, 2020

(87) PCT Pub. No.: WO2020/024078
PCT Pub. Date: Feb. 6, 2020

(65) Prior Publication Data
US 2021/0015780 A1    Jan. 21, 2021

(51) Int. Cl.
*A61K 31/222* (2006.01)
*A61P 1/12* (2006.01)
*A61K 31/09* (2006.01)
*A61K 31/122* (2006.01)
*A61K 31/255* (2006.01)

(52) U.S. Cl.
CPC ............ *A61K 31/222* (2013.01); *A61K 31/09* (2013.01); *A61K 31/122* (2013.01); *A61K 31/255* (2013.01); *A61P 1/12* (2018.01)

(58) Field of Classification Search
CPC .......... A61P 1/12; A61K 31/09; A61K 31/222
See application file for complete search history.

(56) References Cited

FOREIGN PATENT DOCUMENTS

| CN | 1646473 | A | 7/2005 |
|---|---|---|---|
| CN | 105198714 | A | 12/2015 |
| CN | 108434127 | B | 1/2020 |
| EP | 2123277 | A1 | 11/2009 |

OTHER PUBLICATIONS

Chinese-language International Search Report and Written Opinion issued in counterpart CN Application No. PCT/CN2018/097685 dated Apr. 29, 2019 with English translation (fourteen (14) pages).
Yoshimura. Mario et al. 2012. "Diarylheptanoid Sulfates and Related Compounds from Myrica Rubra Bark." Journal of Natural Products., vol. 75, No. 10, pp. 1798-1802.
Whiting, Donald A. et al. 1978. "Cyclization of 1, 7-diarylheptanoids through Oxidative, Reductive, and Photochemical Radical Processes: Total Synthesis of them, m-bridged biaryls myricanone and (±)-myricanol, and a Related Diaryl Ether." Tetrahedron Letters.,vol. /, No. 26, pp. 2335-2338.
Whiting, Donald A. et al. 1980. "Total Syntheses of the meta, meta-bridged biphenyls (±)-myricanol and Myricanone. and of an Isomeric Biphenyl Ether, a 14-oxa[7,1]metaparacyclophane." Journal of the Chemical Society, Perkin Transactions 1: Organic and Bio-Organic Chemistry. vol. /, No. 2, pp. 623-628.
Ibrahim, Sabrin R. M. et al. 2016. "Alnuheptanoid B: A New Cyclic Diarylheptanoid from Alnus Japonica Stem Bark " Records of Natural Products., vol. 10, No. 3, pp. 362-368.
Ko, Ha Na et al. 2017. "Anti-Inflammatory Constituents from the Branches of Pourthiaea villosa (Thunb.) Decne." Bulletin of the Korean Chemical Society., vol. 38, No. 7, pp. 711-715.
Extended European Search Report issued in counterpart EP Appl No. 18928374.0 dated Sep. 14, 2021 (ten (10) pages).
Ya-Chih Ting et al. 2014. "Biological evaluation of secondary metabolites from the roots of Myrica adenophora." Phytochemistry. vol. 103, pp. 89-98.
Japanese-language Office Action issued in counterpart JP Appl. No. 2020-524059 dated Mar. 24, 2021 (six (6) pages).

*Primary Examiner* — Marcos L Sznaidman
(74) *Attorney, Agent, or Firm* — David S. Bradin; Nexsen Pruet, PLLC

(57) ABSTRACT

The present application provides a medicament having an anti-inflammatory bowel disease function, and a preparation method therefor and an application thereof. The medicament has a structure as represented in formula I or formula II. The medicament and a pharmaceutically acceptable salt, a solvate, a prodrug, a tautomer, a stereoisomer, or a pharmaceutical composition thereof provided by the present application have a good effect on inflammatory bowel diseases, can be used for preparing medicaments for treating the inflammatory bowel diseases, and have important clinical significance and wide application prospects.

9 Claims, 14 Drawing Sheets

MEDICAMENT HAVING ANTI-INFLAMMATORY BOWEL DISEASE FUNCTION, AND PREPARATION METHOD THEREFOR AND APPLICATION THEREOF

CROSS REFERENCE TO RELATED APPLICATIONS

This application is a 35 U.S.C. § 371 U.S. national phase entry of International Application No. PCT/CN2018/097685 having an international filing date of Jul. 28, 2018, the contents of which are incorporated herein by reference in their entirety.

TECHNICAL FIELD

The present application belongs to the field of medicine, and relates to a medicament having an anti-inflammatory bowel disease effect, a preparation method thereof, and an application thereof and, in particular, to a myricanol derivative, a preparation method thereof, and an application thereof.

BACKGROUND

Inflammatory bowel disease (IBD) is a group of chronic non-specific intestinal inflammatory diseases whose causes are not very clear, and includes ulcerative colitis (UC) and Crohn's disease (CD). Its pathogenesis is unknown, and the related pathogenic factors that have been found include genetics, infection, environmental pollution, diets, intestinal microecology, etc. The IBD is a common disease in North America and Europe. The prevalence of the ulcerative colitis in Europe and the United States is $240/100,000$, and the incidence thereof is $10/100,000$ to $20/100,000$. The prevalence of the Crohn's disease is $200/100,000$, and the incidence thereof is $5/100,000$ to $10/100,000$. The incidence of the IBD in Japan has gradually increased in the past 30 years. Although there is no epidemiological data of common people in China, the number of patients with this disease has gradually increased in the past ten years, and this tendency is significant. It can be predicted according to statistics of cases from multiple hospitals that the prevalence of the ulcerative colitis is 11.6/100,000, and the incidence thereof is about $3/100,000$; and the prevalence of the Crohn's disease is 1.4/100,000, and the incidence thereof is about 0.4/100,000. There may be more actual cases.

Traditional IBD treatments based on aminosalicylic acids, glucocorticoids, immunosuppressants, biological agents, etc. are still the mainstream. Due to complex causes and poor efficacy, many patients receiving treatments have not been relieved, and up to 80% of patients of the Crohn's disease and up to 30% of UC patients will eventually need to undergo surgery. A huge medical demand is to be satisfied in the field. In recent years, clinical trials and applications of faecal microbiota transplantation have been developing and need to be further explored since patients accept this to a low degree. Therefore, it is still an urgent problem to be solved in clinics to find a safe and reliable IBD medicament that can enter the intestines to exert a significant therapeutic effect, effectively reduce an ulcerative area, relieve symptoms of patients, and does not cause drug resistance.

Bayberry is a plant belongs to the genus *Myrica* in the family Myricae and widely planted in China, and has a long history. The traditional Chinese medicine records that a bark of the bayberry tastes bitter, is warm in nature, has the effects of removing blood stasis, stopping bleeding and relieving pains, and is used by folk for treating bruises, fractures, dysentery, gastric and duodenal ulcers, toothaches, etc. Myricanol is a typical macrocyclic biphenyl-based cyclic diarylheptane compound extracted from the bark of the bayberry, and has a structure represented by Formula III. Due to its unique chemical structure, this kind of compounds has drawn wide attention in recent years. Currently, it is reported that studies on the pharmacological activity of myricanol mainly involve anti-virus, anti-tumor, anti-oxidation, free radical scavenging, immune regulation, anti-allergy and other aspects, which shows its wide potential uses.

CN102552243A has disclosed an application of myricanol and/or myricetone to the preparation of anti-tumor medicaments. The anti-tumor medicaments include medicaments for preventing and/or treating liver cancer, medicaments for preventing and/or treating lung cancer, medicaments for preventing and/or treating leukemia, medicaments for preventing and/or treating gastric cancer, or medicaments for preventing and/or treating other tumors. This application only discloses the application of myricanol in the aspect of anti-tumor, and is limited to a use thereof as medicaments for treating tumors.

CN105198714A has disclosed a myricanol derivative, a preparation method thereof, and an application thereof to anti-tumor. The myricanol derivative has the following structure:

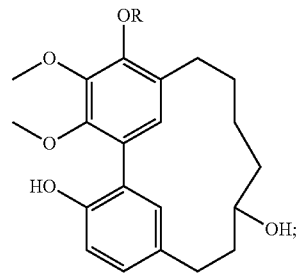

where R is substituted benzyl. The myricanol derivative is obtained through a substitution reaction between myricanol as a raw material and substituting benzyl at room temperature under an alkaline condition. For the application of the myricanol derivative in the preparation of anti-tumor medicaments, a prodrug obtained by introducing a benzyl group which is substituted by F, Cl, Br, CN, $NO_2$, Me, or OMe at the para position into the hydroxyl at position 5 of myricanol may be slowly hydrolyzed in body to release a parent drug, thereby prolonging efficacy and action time, improving bioavailability, and further enhancing anti-tumor activity. However, the myricanol derivative prepared by this method is only limited to anti-tumor applications.

U.S. Pat. No. 8,940,945B2 has disclosed a method and material for reducing Tau protein, and a method for treating a neurodegenerative disease, and provides a myricanol compound. In an embodiment, a myricanol derivative is separated from a plant in the genus Ricin and applied to the treatment of the neurodegenerative disease. The myricanol and derivatives thereof disclosed by this application are only limited to applications in the neurodegenerative disease.

At present, there is no relevant studies and reports on an application of myricanol and its derivative in the aspect of the IBD. To better apply myricanol to this particular disease, myricanol is modified based on a certain structure-effect relationship. The modification of the myricanol derivative aims to improve activity and/or druggability thereof, so that medication requirements of the treatment and prevention of the IBD can be better satisfied.

SUMMARY

An object of the present application is to provide a medicament having an anti-inflammatory bowel disease effect, a preparation method thereof, and an application thereof.

To achieve the object, the present application adopts solutions below.

In a first aspect, the present application provides a medicament having an anti-inflammatory bowel disease effect, having a structure represented by Formula I or Formula II:

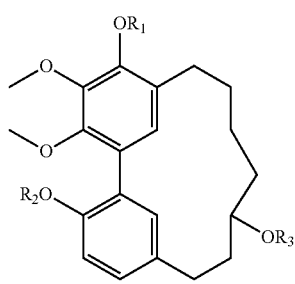

Formula I

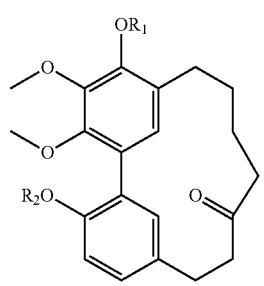

Formula II where $R_1$ and $R_2$ are each independently selected from any one of hydrogen, ethyl, n-propyl, n-butyl, isopropyl, allyl, isobutyl, t-butyl, benzyl, acetyl, a sulfonic acid group, a phosphoric acid group, a benzoic acid group, a benzamido group, a benzoylcyclopropylamino group, a benzenesulfonic acid group, a picolinamido group, a picolinoylcyclopropylamino group, a pyrimidinecarboxamido group, or a cyclopropylpyrimidinecarboxamido group;

$R_3$ is selected from any one of hydrogen, acetyl, a sulfonic acid group, or a phosphoric acid group; and in Formula I, $R_1$, $R_2$, and $R_3$ are not hydrogen at the same time; $R_1$, $R_2$, and $R_3$ are not acetyl at the same time; and $R_1$ and $R_2$ are not benzyl at the same time; and in Formula II, $R_1$ and $R_2$ are not hydrogen or benzyl at the same time.

The medicament having an anti-inflammatory bowel disease effect provided by the present application can inhibit the expression of COX2 protein associated with IBD, has a strong ability to inhibit inflammatory factor $PGE_2$, can effectively reduce the ulcerative area and relieve symptoms of the IBD, has no obvious toxic side effects, and is safe and reliable.

Compared with use of myricanol and its derivative in the anti-tumor aspect in an existing method, the medicament having an anti-inflammatory bowel disease effect provided by the present application has developed a brand-new use, which greatly expands the application range of myricanol derivatives.

The COX2 is an inducible enzyme, can be induced by a variety of cytokines and inflammatory transmitters, and is closely related to the occurrence of inflammation. It has been reported that COX2 is mostly not expressed under normal physiological conditions, and the expression amount of COX2 significantly increases under some pathological conditions (such as a gastric ulcer, the IBD, and colon cancer). $PGE_2$ is an important inflammatory factor downstream of COX2.

Preferably, the medicament has any one of the following compound structures A to J:

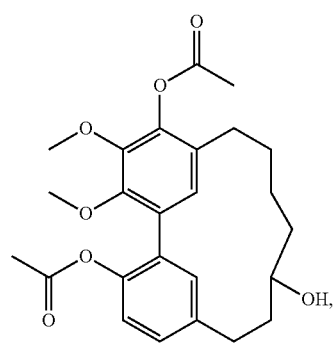

A

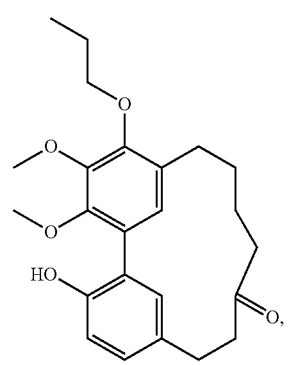

B

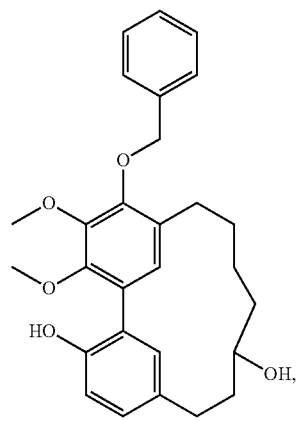

C

D
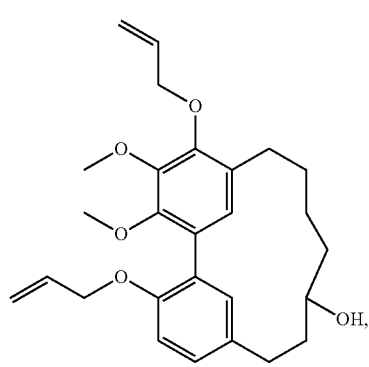
E
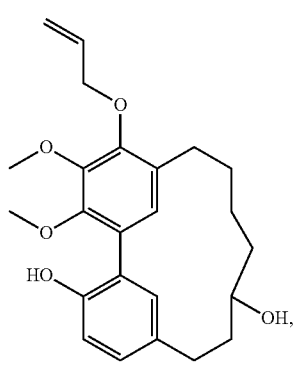
F
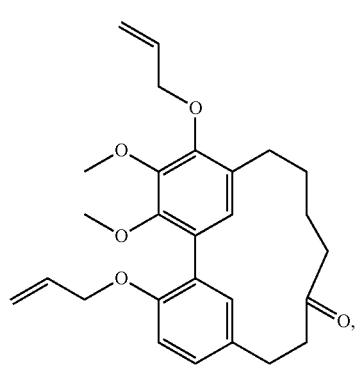
G
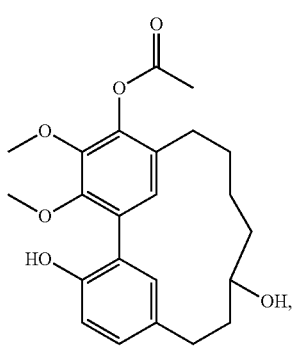
H
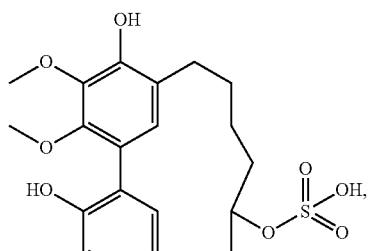
I
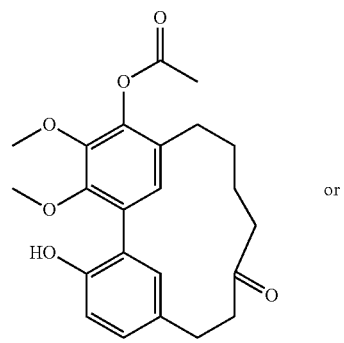
or
J
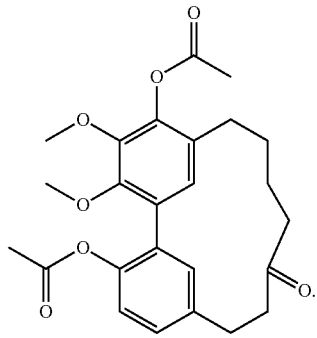
Preferably, the structure of the medicament having an anti-inflammatory bowel disease effect is any one of -continued

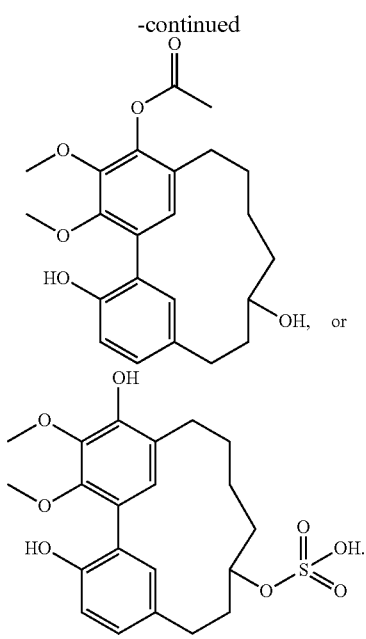

In the present application, myricanol derivatives which preferably have the above three structures inhibit the expression of COX2 protein at a higher rate, inhibit the inflammatory factor $PGE_2$ at a higher rate which can reach 100%, and has a better anti-inflammatory effect compared with other myricanol derivatives.

In a second aspect, the present application provides a preparation method of a medicament having an anti-inflammatory bowel disease effect and having a structure represented by Formula I, wherein the method includes:

performing a substitution reaction on a compound represented by Formula III, which is myricanol, and a nucleophile in the presence of an alkaline reagent to obtain a compound represented by Formula I, where a reaction equation is as follows:

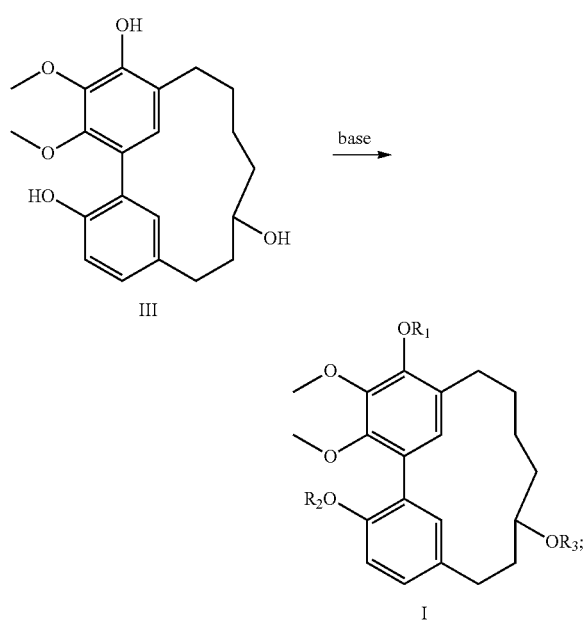

where $R_1$ and $R_2$ are each independently selected from any one of hydrogen, ethyl, n-propyl, n-butyl, isopropyl, allyl, isobutyl, t-butyl, benzyl, acetyl, a sulfonic acid group, a phosphoric acid group, a benzoic acid group, a benzamido group, a benzoylcyclopropylamino group, a benzenesulfonic acid group, a picolinamido group, a picolinoylcyclopropylamino group, a pyrimidinecarboxamido group, or a cyclopropylpyrimidinecarboxamido group;

$R_3$ is selected from any one of hydrogen, acetyl, a sulfonic acid group, or a phosphoric acid group; and $R_1$, $R_2$, and $R_3$ are not hydrogen at the same time; $R_1$, $R_2$, and $R_3$ are not acetyl at the same time; and $R_1$ and $R_2$ are not benzyl at the same time.

In the present application, the nucleophile is a halide or an acid anhydride having a same group as $R_1$, $R_2$, and $R_3$, and it is reacted to obtain the structure represented by Formula I. Those skilled in the art may select the nucleophile according to the structure represented by Formula I.

Preferably, the alkaline reagent includes any one or a combination of at least two of pyridine, triethylamine, N,N-diisopropylethylamine, N-methylmorpholine, potassium carbonate, sodium carbonate, cesium carbonate, potassium hydroxide, sodium hydroxide, or potassium t-butoxide, preferably pyridine or triethylamine.

In the present application, the alkaline reagent is not limited to the reagents listed above, and may be any alkaline reagent which can provide an alkaline environment and facilitate a forward progress of the reaction.

Preferably, a molar ratio of the compound represented by Formula III, which is myricanol, to the nucleophile is 1:(1-6), which may be, for example, 1:1, 1:2, 1:3, 1:4, 1:5, or 1:6.

In the present application, the molar ratio of the compound represented by Formula III, which is myricanol, to the nucleophile determines the process of the substitution reaction. Since different nucleophiles have different steric hindrance and electronic effects, the priority order of $R_1$, $R_2$, and $R_3$ in the substitution reactions is generally $R_1>R_2>R_3$. However, if the substitution reagent corresponding to the substituent is an acyl halide, the priority order is $R_3>R_1>R_2$. In the present application, by controlling a feed ratio of myricanol to the nucleophile during the reaction, a mono- or multi-substituted reaction product can be obtained.

An example may be as follows: when the reaction order is $R_1>R_2>R_3$, myricanol is reacted with acetic anhydride, and the molar ratio for the reaction is controlled to be about 1:2, only substitutions at positions $R_1$ and $R_2$ occur, and

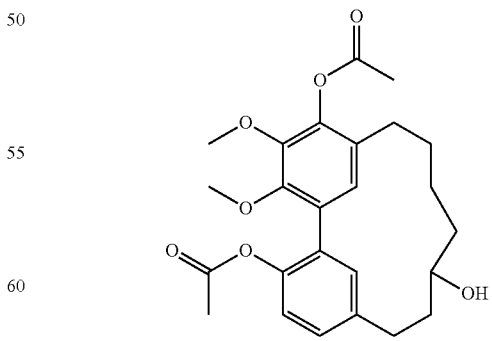

can be obtained; when myricanol is reacted with allyl bromide, and the molar ratio for the reaction is controlled to be 1:1, only a substitution at position $R_1$ occurs, and the obtained compound is

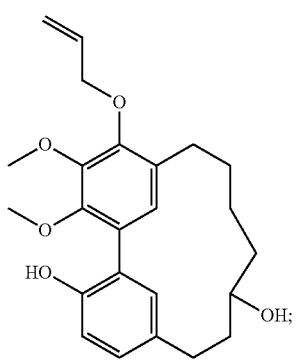 [SMILES: C=CCOc1c2cc(c(OC)c1OC)-c1cc(ccc1O)CCC(O)CCCC2]

when the reaction order is $R_3>R_1>R_2$, myricanol is reacted with chlorosulfonic acid, and the molar ratio for the reaction is controlled to be about 1:1, only a substitution at position $R_3$ occurs, and the obtained compound is

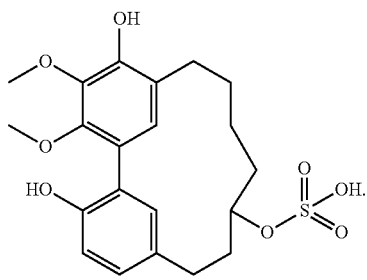 [SMILES: COc1c2cc(c(O)c1OC)CCCCC(OS(=O)(=O)O)CCc1ccc(O)c-2c1]

Preferably, a solvent for the substitution reaction includes any one or a combination of at least two of dichloromethane, tetrahydrofuran, acetonitrile, pyridine, or triethylamine.

Preferably, the substitution reaction is performed at a temperature of 0-80° C., which may be, for example, 0° C., 5° C., 10° C., 15° C., 20° C., 25° C., 30° C., 35° C., 40° C., 45° C., 50° C., 55° C., 60° C., 65° C., 70° C., 75° C., or 80° C., etc.

Preferably, the substitution reaction lasts for 1-30 h, which may be, for example, 1 h, 5 h, 10 h, 15 h, 20 h, 25 h, or 30 h, etc.

In addition, the present application further provides a preparation method of a medicament having an anti-inflammatory bowel disease effect and having a structure represented by Formula I, wherein the method includes:

performing an oxidation reaction on a compound represented by Formula IV in the presence of an oxidant to obtain a compound represented by Formula II, where a reaction equation is as follows:

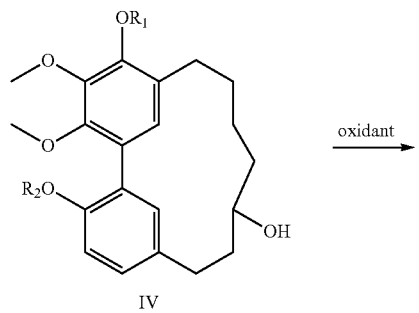

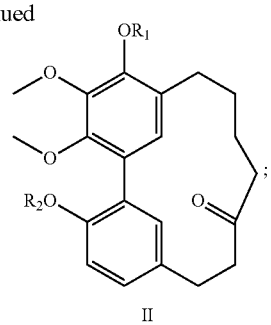

where $R_1$ and $R_2$ are each independently selected from any one of hydrogen, ethyl, n-propyl, n-butyl, isopropyl, allyl, isobutyl, t-butyl, benzyl, acetyl, a sulfonic acid group, a phosphoric acid group, a benzoic acid group, a benzamido group, a benzoylcyclopropylamino group, a benzenesulfonic acid group, a picolinamido group, a picolinoylcyclopropylamino group, a pyrimidinecarboxamido group, or a cyclopropylpyrimidinecarboxamido group; and $R_1$ and $R_2$ are not hydrogen or benzyl at the same time.

Preferably, a molar ratio of the compound represented by Formula IV to the oxidant is 1:(0.5-5), which may be, for example, 1:0.5, 1:1, 1:1.5, 1:2, 1:2.5, 1:3, 1:3.5, 1:4, 1:4.5, or 1:5, etc.

Preferably, the oxidant includes any one or a combination of at least two of pyridinium chlorochromate, chromium trioxide, ozone, hydrogen peroxide, or sulfur trioxide.

Preferably, a solvent for the oxidation reaction includes any one or a combination of at least two of dichloromethane, tetrahydrofuran, toluene, N,N-dimethylformamide, n-heptane, or dimethyl sulfoxide.

Preferably, the oxidation reaction is performed at a temperature of 0-50° C., which may be, for example, 0° C., 5° C., 10° C., 15° C., 20° C., 25° C., 30° C., 35° C., 40° C., 45° C., or 50° C., etc.

Preferably, the oxidation reaction lasts for 1-10 h, which may be, for example, 1 h, 2 h, 3 h, 4 h, 5 h, 6 h, 7 h, 8 h, 9 h, or 10 h.

In a third aspect, the present application provides a pharmaceutically acceptable salt of the medicament having an anti-inflammatory bowel disease effect as described in the first aspect.

Preferably, the pharmaceutically acceptable salt is a metal salt of a compound represented by Formula I or a metal salt of a compound represented by Formula II.

Preferably, the metal salt includes any one of a lithium salt, a sodium salt, a potassium salt, a magnesium salt, or a calcium salt, preferably a sodium salt or a potassium salt.

In a fourth aspect, the present application provides a solvate of the medicament having an anti-inflammatory bowel disease effect as described in the first aspect.

Preferably, the solvate is a hydrate of a compound represented by Formula I, an alcoholate of the compound represented by Formula I, a hydrate of a compound represented by Formula II, or an alcoholate of the compound represented by Formula II.

In a fifth aspect, the present application provides a tautomer or a stereochemical isomer of the medicament having an anti-inflammatory bowel disease effect as described in the first aspect.

In the present application, the tautomer refers to cis-trans isomerization of a double bond in a chemical structure, and the stereochemical isomer refers to isomerization of each chiral center in the $R_3$ group.

In a sixth aspect, the present application provides a prodrug of the medicament having an anti-inflammatory bowel disease effect as described in the first aspect.

In the present application, the prodrug having an anti-inflammatory bowel disease effect is inactive or less active in vitro and undergoes metabolic changes in vivo to release a myricanol derivative with activity, thereby taking effect.

In a seventh aspect, the present application provides a pharmaceutical composition, including the medicament having an anti-inflammatory bowel disease effect as described in the first aspect.

Preferably, the pharmaceutical composition further includes an adjuvant.

Preferably, the adjuvant includes any one or a combination of at least two of an excipient, a diluent, a carrier, a flavoring agent, a binder, or a filler.

Preferably, a preparation of the anti-inflammatory pharmaceutical composition includes any one of an oral preparation, an external preparation, or a parenteral preparation.

For example, in the present application, the pharmaceutical composition may be prepared into solid, semi-solid, liquid, or gas preparations, such as tablets, pills, capsules, powders, granules, ointments, emulsions, suspensions, suppositories, injections, inhalations, gels, microspheres, and aerosols. A typical means for administering the compound, the pharmaceutically acceptable salt thereof, or the pharmaceutical composition thereof in the present application includes, but is not limited to, oral, rectal, topical, inhalation, parenteral, sublingual, intravaginal, intranasal, intraocular, intraperitoneal, intramuscular, subcutaneous, and intravenous administration.

In an eighth aspect, the present application provides use of the medicament having an anti-inflammatory bowel disease effect as described in the first aspect, the pharmaceutically acceptable salt of the medicament having an anti-inflammatory bowel disease effect as described in the third aspect, the solvate of the medicament having an anti-inflammatory bowel disease effect as described in the fourth aspect, the tautomer or the stereochemical isomer of the medicament having an anti-inflammatory bowel disease effect as described in the fifth aspect, the prodrug having an anti-inflammatory bowel disease effect as described in the sixth aspect, or the pharmaceutical composition as described in the seventh aspect in the preparation of a medicament for treating an inflammatory bowel disease.

Compared with the existing art, the present application has beneficial effects below.

The medicament having an anti-inflammatory bowel disease effect, the pharmaceutically acceptable salt, the solvate, the prodrug, the tautomer, or the stereochemical isomer thereof, or the pharmaceutical composition provided by the present application has a good effect on the inflammatory bowel disease and can be developed as a medicating for preventing and treating the inflammatory bowel disease. The medicament having an anti-inflammatory bowel disease effect provided by the present application has good drugability, can effectively reduce the ulcerative area and relieve symptoms of the inflammatory bowel disease, and is safe and reliable. For the inflammatory bowel disease whose symptoms need to be relieved and improved, the medicament having an anti-inflammatory bowel disease effect has more clinical significance and a broad application prospect.

DETAILED DESCRIPTION

The solutions of the present application are further described below through specific examples. Those skilled in the art should understand that the examples described herein are merely used for a better understanding of the present application and should not be construed as specific limitations to the present application.

Example 1

In this example, 5,17-diacetoxy myricanol was prepared by a method below.

Figure 1:
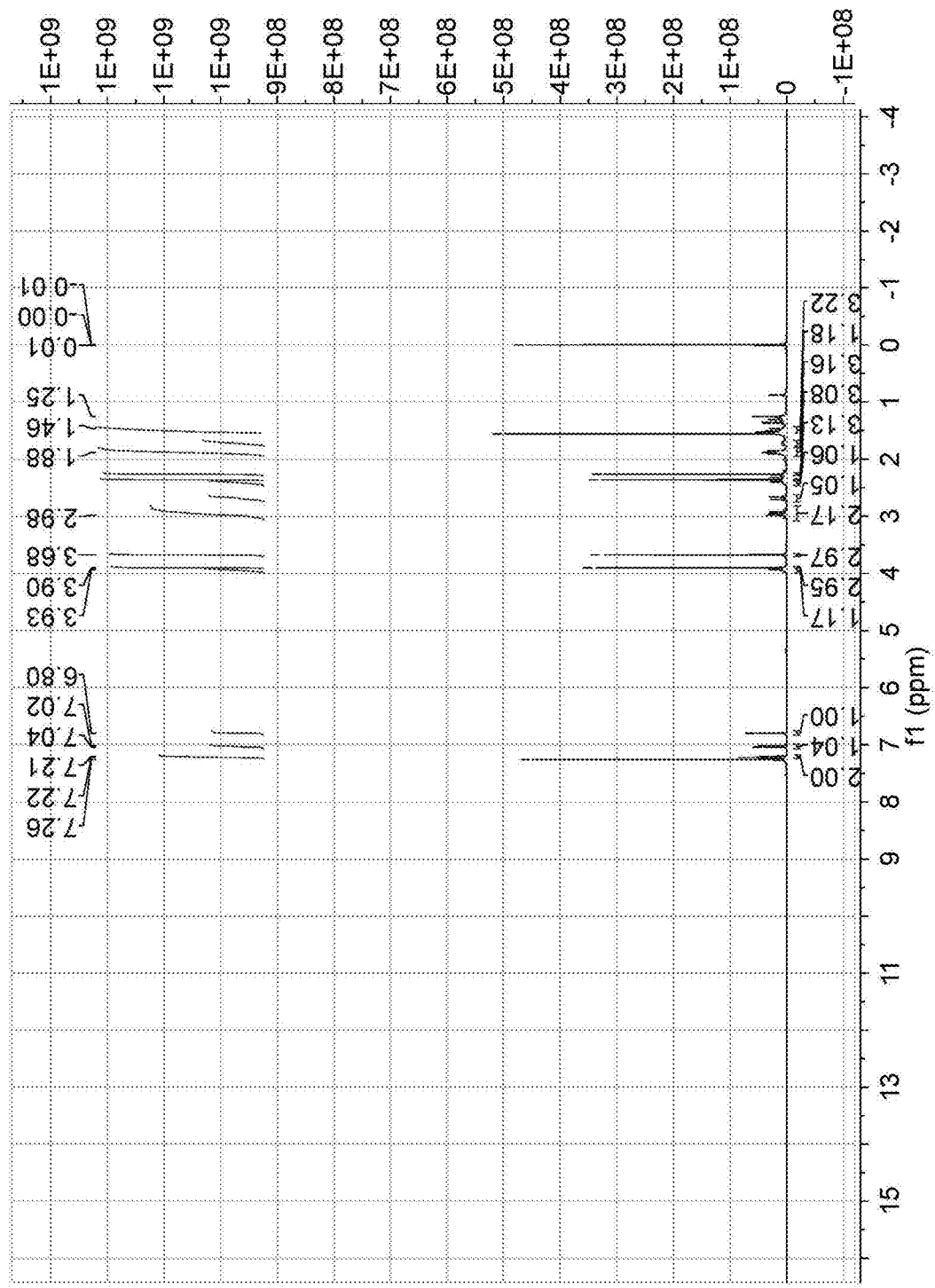
FIG. 1 is a 1H NMR diagram of compound A in Example 1 of the present application.

Under the protection of nitrogen, myricanol (0.49 g, 1.37 mmol), dichloromethane (30 mL), and pyridine (0.32 g, 4.10 mmol) were added in sequence into a 100 mL eggplant-shaped flask; acetic anhydride (0.31 g, 2.20 mmol) was diluted with dichloromethane (20 mL), placed in a pressure-equalizing dropping funnel, slowly added dropwise into the eggplant-shaped flask, and reacted. The dropwise addition was finished in about 30 min. The system was transferred to an oil bath at 60° C. and refluxed for 3 h. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5,17-diacetoxy myricanol (white solid A, 0.35 g, LC-MS: m/z=443.1 (M+1)$^+$, purity: 99.36%) with a yield of 58%. The proton nuclear magnetic resonance spectrum thereof is shown in FIG. 1.

Example 2

In this example, 5-n-propoxy myricanol was prepared by a method below.

Under the protection of nitrogen, myricanone (0.36 g, 1.01 mmol), N,N-dimethylformamide (10 mL), 1-chloropropane (0.17 g, 2.21 mmol), and potassium carbonate (0.42 g, 3.01 mmol) were added in sequence into a 100 mL eggplant-shaped flask. The system was reacted for 3 h in an oil bath at 100° C. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5-n-propoxy myricanol (white solid B, 0.28 g, LC-MS: m/z=395.6 (M–H)$^-$, 99.38%) with a yield of 70%.

Example 3

In this example, 5-benzyloxy myricanol was prepared by a method below.

Under the protection of nitrogen, myricanol (0.36 g, 1.00 mmol), acetonitrile (10 mL), benzyl bromide (0.38 g, 2.21 mmol), and potassium carbonate (0.42 g, 3.01 mmol) were added in sequence into a 100 mL eggplant-shaped flask. The system was reacted for 6 h in an oil bath at 80° C. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5-benzyloxy myricanol (white solid C, 0.20 g, LC-MS: m/z=447.6 (M–H)$^-$, 98.09%) with a yield of 62%.

Example 4

In this example, 5,17-diallyloxy myricanol was prepared by a method below.

Under the protection of nitrogen, myricanol (0.36 g, 1.00 mmol), acetonitrile (10 mL), allyl bromide (0.27 g, 2.21 mmol), and potassium carbonate (0.42 g, 3.01 mmol) were added in sequence into a 100 mL eggplant-shaped flask. The system was reacted for 6 h in an oil bath at 80° C. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5,17-diallyloxy myricanol (white solid D, 0.35 g, LC-MS: m/z=439.6 (M–H)$^-$, 99.70%) with a yield of 79%.

Example 5

In this example, 5-allyloxy myricanol was prepared by a method below.

Under the protection of nitrogen, myricanol (0.36 g, 1.00 mmol), acetonitrile (10 mL), allyl bromide (0.13 g, 1.10 mmol), and potassium carbonate (0.42 g, 3.01 mmol) were added in sequence into a 100 mL eggplant-shaped flask. The system was reacted for 6 h in an oil bath at 60° C. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5-allyloxy myricanol (white solid E, 0.22 g, LC-MS: m/z=399.2 (M+H)$^+$, 96.64%) with a yield of 55%.

Example 6

In this example, 5,17-allyloxy myricanone was prepared by a method below.

5,17-Diallyloxy myricanol (1.20 g, 2.74 mmol) was weighted and dissolved in dichloromethane (50 mL), added with pyridinium chlorochromate (2.95 g, 13.69 mmol), and reacted for 1 h under the protection of argon. TLC (PE:EA=3:1) showed that raw materials disappeared, and then the reaction was stopped. The reaction solution was concentrated to obtain a light brown solid. The light brown solid was subjected to gradient elution by using fast preparative column chromatography (petroleum ether-ethyl acetate: 0-35%) to obtain 5,17-allyloxy myricanone (white solid F, 0.71 g, LC-MS: m/z=436.6 (M+H)$^+$, 94.53%) with a yield of 59%.

Example 7

In this example, 5-acetoxy myricanol was prepared by a method below.

Figure 2:
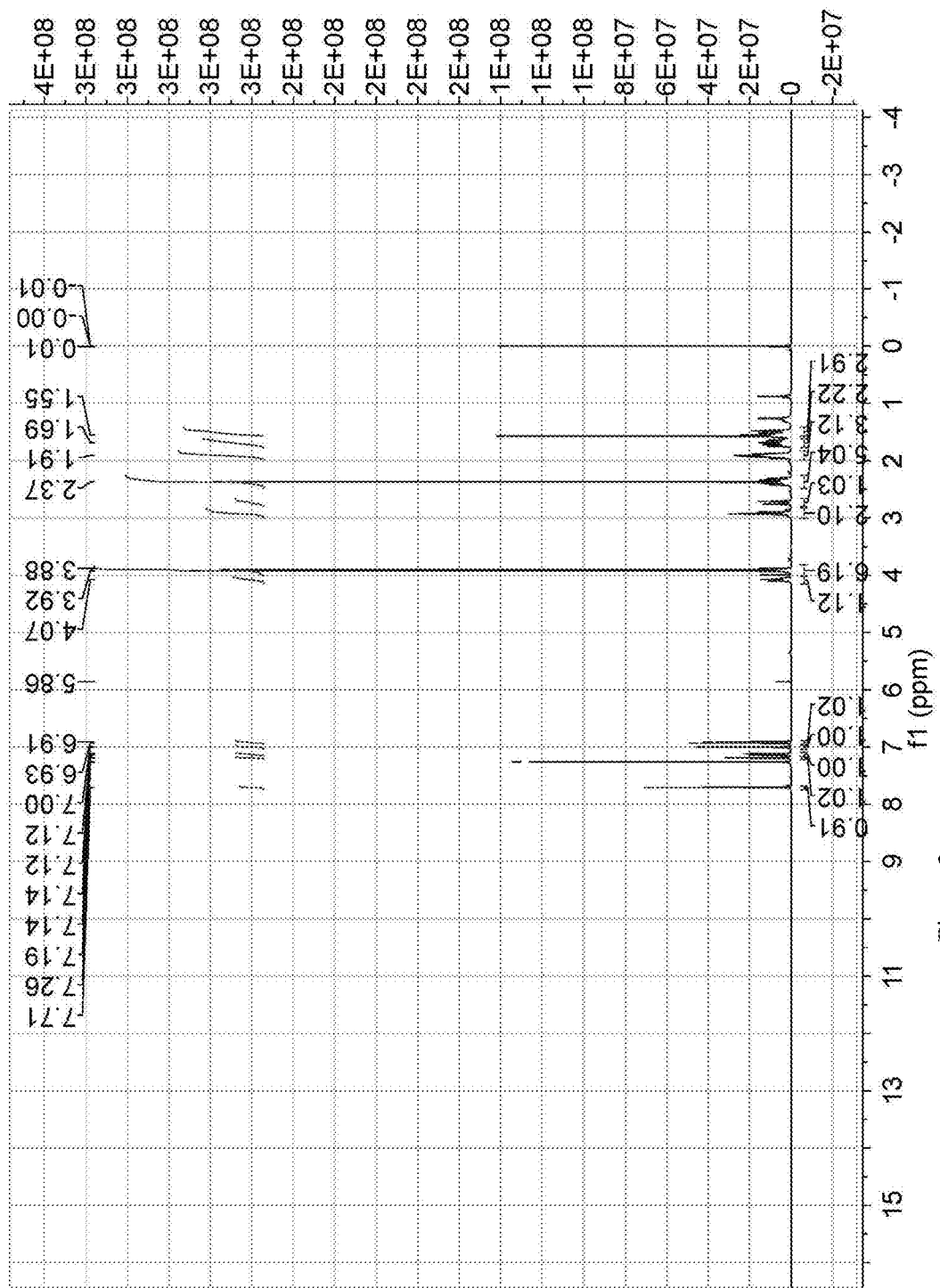
FIG. 2 is a 1H NMR diagram of compound G in Example 7 of the present application.

Under the protection of nitrogen, myricanol (0.49 g, 1.37 mmol), dichloromethane (30 mL), and pyridine (0.32 g, 4.10 mmol) were added in sequence into a 100 mL eggplant-shaped flask; acetic anhydride (0.16 g, 1.10 mmol) was diluted with dichloromethane (20 mL), placed in a pressure-equalizing dropping funnel, slowly added dropwise into the eggplant-shaped flask, and reacted. The dropwise addition was finished in about 30 min. The system was transferred to an oil bath at 60° C. and refluxed for 3 h. The reaction solution was sent for LC-MS analysis. The reaction solution was separated through gradient elution by using preparative liquid chromatography (mobile phase: petroleum ether-ethyl acetate: 0-35%). The received liquids were combined, and solvents were removed through rotary evaporation to obtain 5-acetoxy myricanol (white solid G, 0.32 g, LC-MS: m/z=400.7 (M+H)$^+$, 94.67%), with a yield of 80%. The proton nuclear magnetic resonance spectrum thereof is shown in FIG. 2.

Example 8

In this example, 11-sulfonyloxy myricanol was prepared by a method below.

Figure 3:
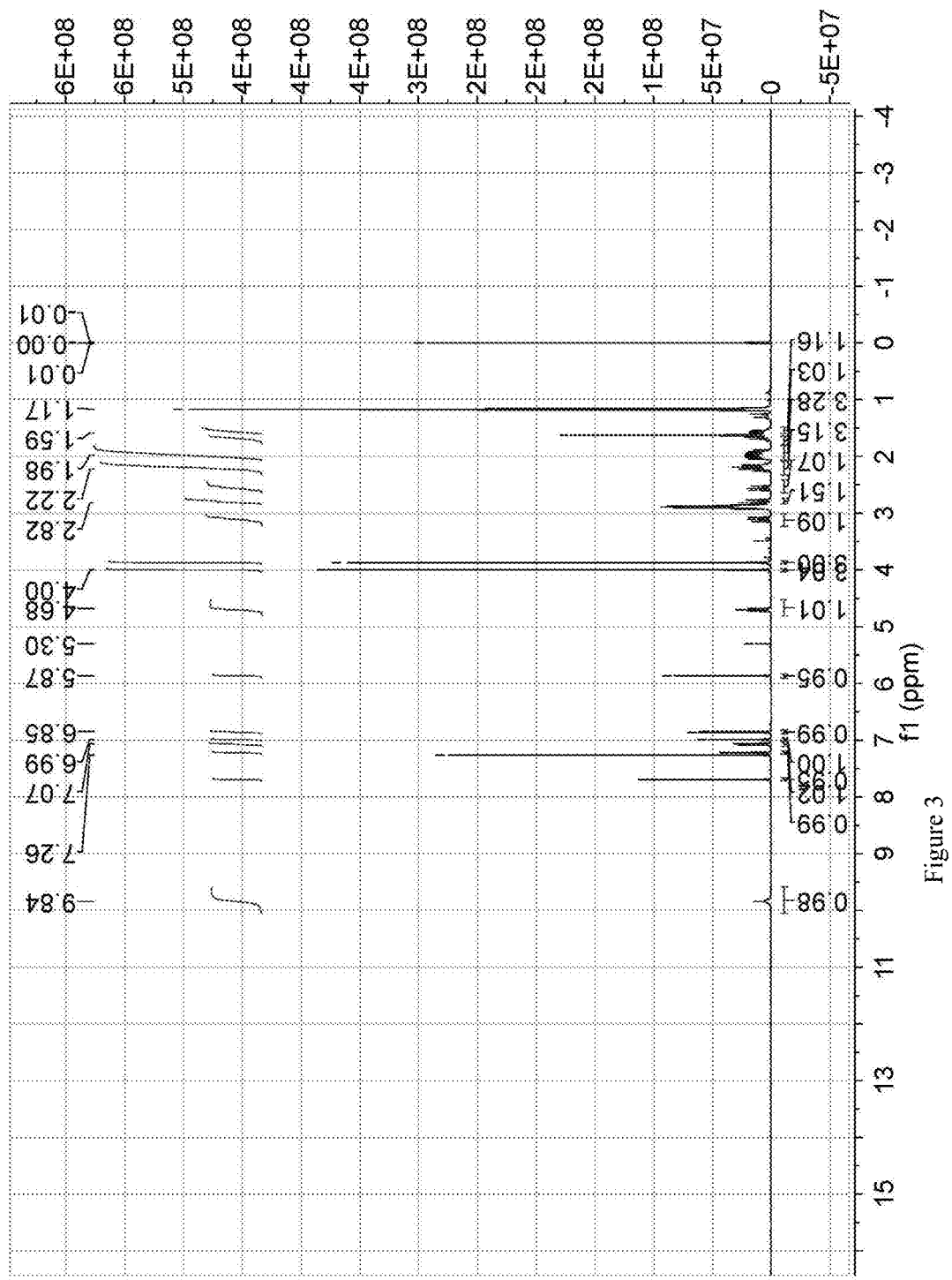
FIG. 3 is a 1H NMR diagram of compound H in Example 8 of the present application.
Figure 4A:
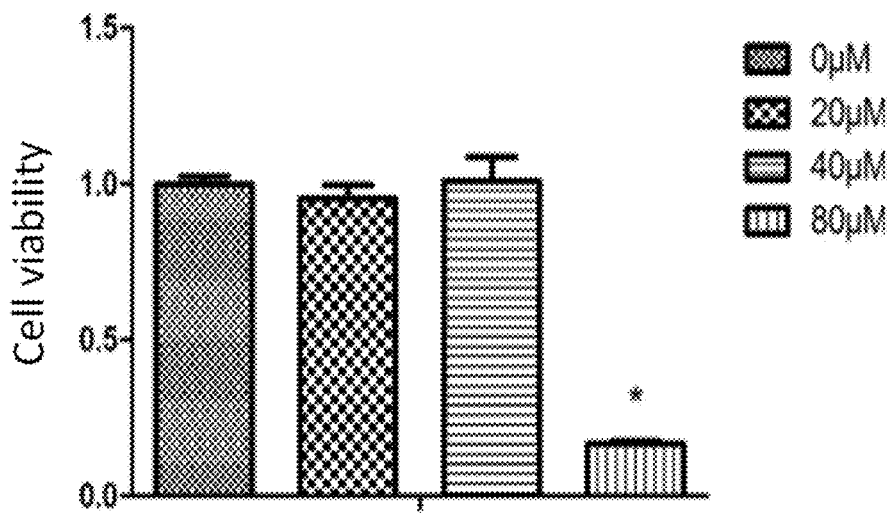
FIG. 4A is a diagram illustrating an effect of compound A on proliferation activity of mouse macrophages RAW264.7 in Example 10 of the present application.
Figure 4B:
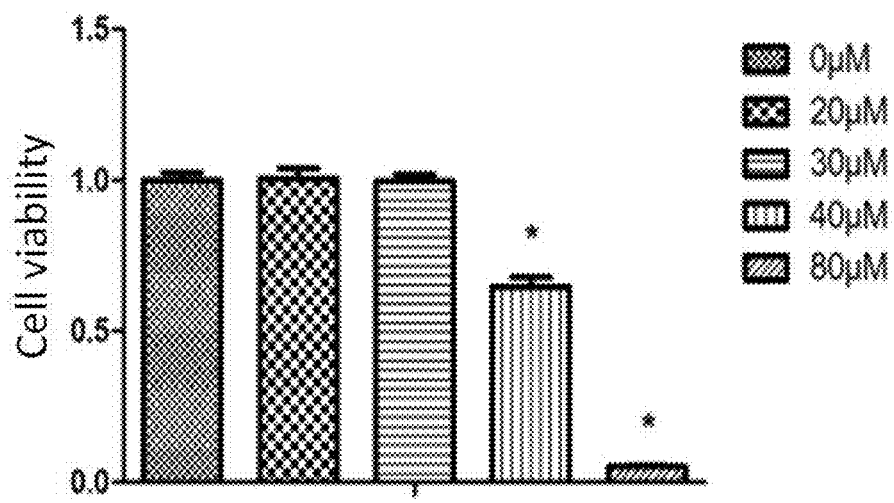
FIG. 4B is a diagram illustrating an effect of compound B on proliferation activity of mouse macrophages RAW264.7 in Example 10 of the present application.
Figure 4C:
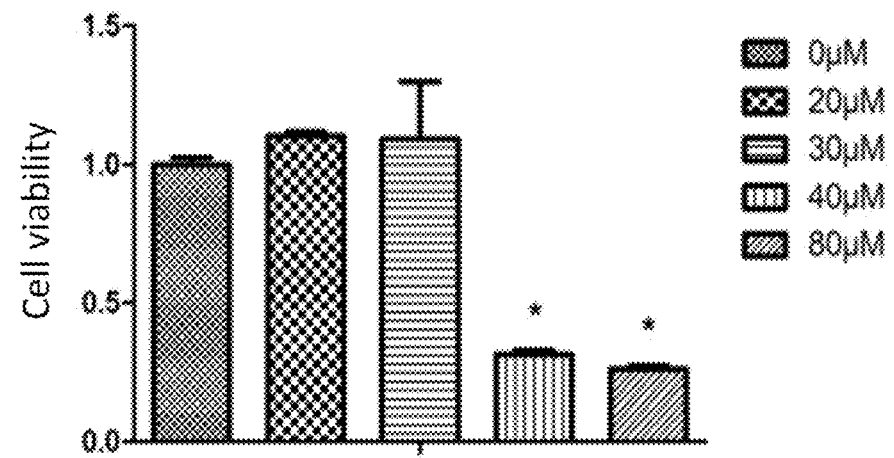
FIG. 4C is a diagram illustrating an effect of compound C on proliferation activity of mouse macrophages RAW264.7 in Example 10 of the present application.
Figure 4D:
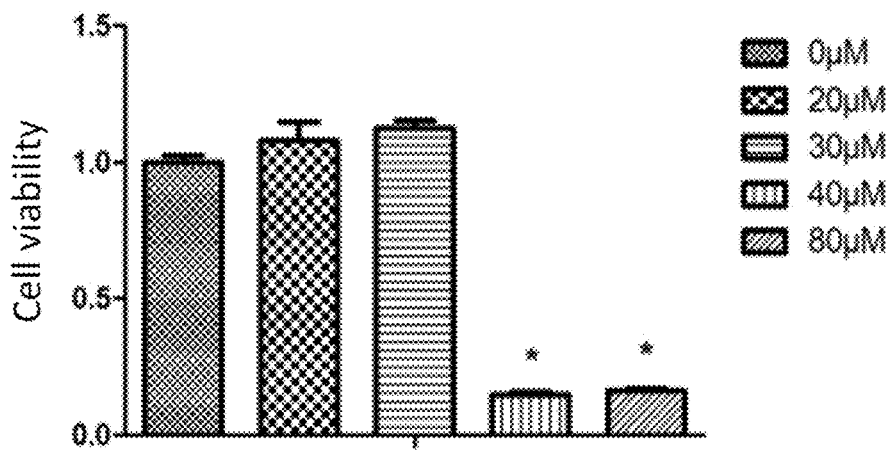
FIG. 4D is a diagram illustrating an effect of compound D on proliferation activity of mouse macrophages RAW264.7 in Example 10 of the present application.
Figure 4E:
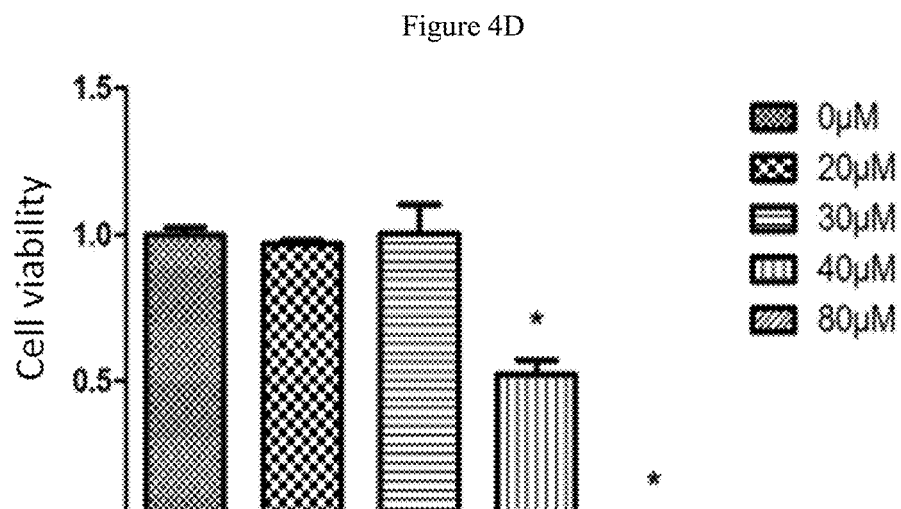
FIG. 4E is a diagram illustrating an effect of compound E on proliferation activity of mouse macrophages RAW264.7 in Example 10 of the present application.
Figure 4F:
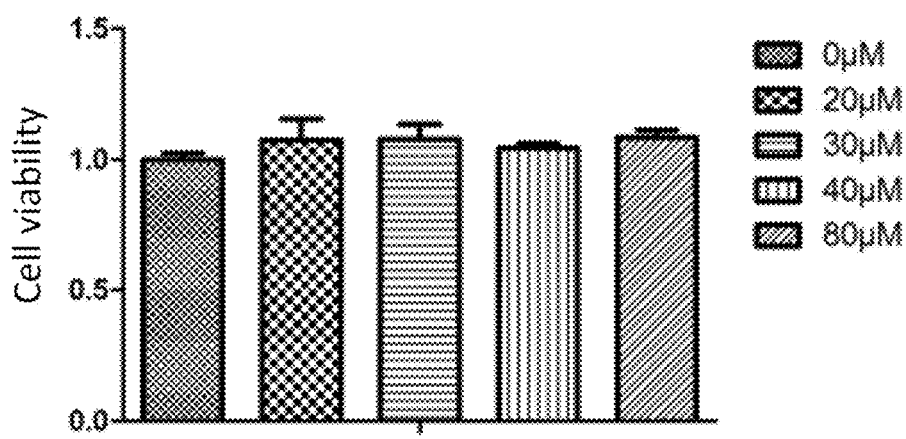
FIG. 4F is a diagram illustrating an effect of compound F on proliferation activity of mouse macrophages RAW264.7 in Example 10 of the present application.
Figure 4G:
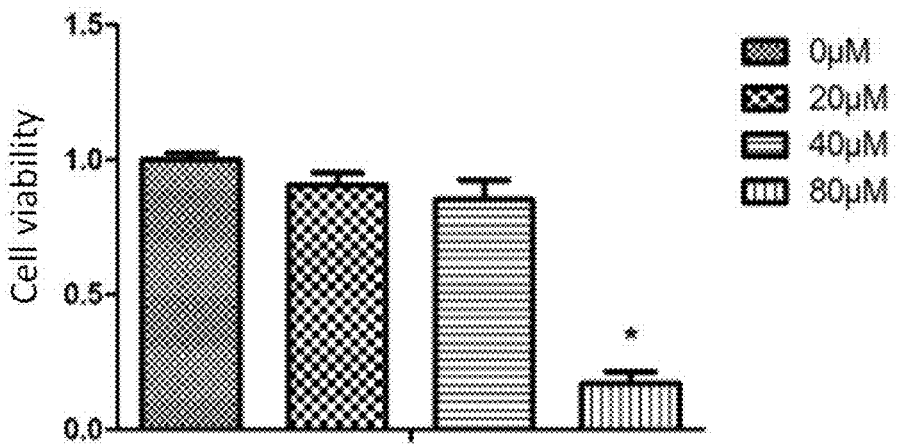
FIG. 4G is a diagram illustrating an effect of compound G on proliferation activity of mouse macrophages RAW264.7 in Example 10 of the present application.
Figure 4H:
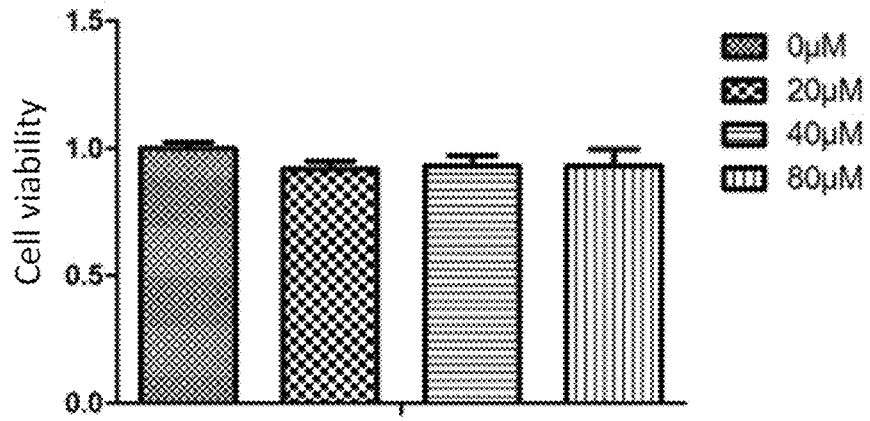
FIG. 4H is a diagram illustrating an effect of compound H on proliferation activity of mouse macrophages RAW264.7 in Example 10 of the present application.

Myricanol (0.36 g, 1.00 mmol) was weighted and dissolved in dichloromethane (20 mL), and added with triethylamine (0.24 g, 3.01 mmol). After an ice bath, a solution of chlorosulfonic acid (0.18 g, 1.51 mmol) in dichloromethane (10 mL) was added dropwise in 15 min and reacted for more than 16 h. TLC (PE:EA=3:1) showed that raw materials disappeared. Silica gel (100-200 mesh, 3 g) was added and mixed with the reaction solution which was subjected to gradient elution by using fast preparative column chromatography (mobile phase: dichloromethane-MeOH: 0-15%), and solvates were removed through rotary evaporation to obtain 11-sulfonyloxy myricanol (white solid H, 0.38 g, LC-MS: m/z=436.7 (M−H)$^-$, 97.82%) with a yield of 86%. The proton nuclear magnetic resonance spectrum thereof is shown in FIG. 3.

Example 9

In this example, 5,17-diacetoxy myricanone was prepared by a method below.

5,17-Diacetoxy myricanol (0.36 g, 1.00 mmol) was dissolved in dichloromethane (10 mL), added with pyridinium chlorochromate (1.29 g, 6.00 mmol), and reacted for 1 h under the protection of argon. TLC (PE:EA=5:1) showed that raw materials disappeared, and then the reaction was stopped. The reaction solution was concentrated to obtain a light brown solid. The light brown solid was subjected to gradient elution by using fast preparative column chromatography (petroleum ether-ethyl acetate: 0-35%) to obtain 5,17-diacetoxy myricanone (white solid J, 0.32 g, LC-MS: m/z=463.2 (M+23)$^+$, 94.53%) with a yield of 94%.

Example 10

In this example, compounds A to H prepared in Examples 1 to 8 were tested for in vitro anti-inflammatory activity.

Effects of myricanol derivatives on the expression of inflammatory factors such as IL-6, TNF-α, PEG$_2$ secreted by a mouse macrophage cell strain RAW 264.7 induced by bacterial lipopolysaccharide (hereinafter referred to as LPS) stimulus: A pre-prepared cell suspension was inoculated in a 96-well plate at 15000 cells/well and 100 μl/well and cultured overnight in an incubator with 5% $CO_2$ at 37° C. At 80% cell confluence, the original culture medium was discarded, and each well was added with 100 μl of prepared drug solution to be tested with a different concentration, cultured for 1 h, and then added with a LPS solution, where the final concentration of LPS in the culture system was 100 ng/mL. Each concentration was set with 3 parallel wells, and a cell control group (no drug and no solvent) and a blank medium control group (no cells, a well for zero adjustment) were set. They were cultured for another 24 h. Cell culture supernatants were aspirated, and an R&D ELISA detection kit (M6000B; MTA00B; VAL601) was used for detecting the expression of the inflammatory factors such as IL-6, TNF-α, and PEG$_2$ in each group. Cell proteins were collected, and a Waters Blot method was used for detecting COX-2 protein expression in each group.

FIG. 4 shows the effects of the myricanol derivatives (i.e., compounds A to H) on proliferation activity of mouse macrophages RAW 264.7. It can be seen from results in FIG. 4 that some compounds A (40 μM), B (30 μM), C (30 μM), D (30 μM), E (30 μM), F (80 μM), G (40 μM), and H (80 μM) have no significant effects on the proliferation activity of the mouse macrophages RAW264.7 (n=3), and the subsequent anti-inflammatory activity assays were carried out at such drug concentrations or below.

In cell experiments, n is the number of experiments, each with 3 repetitive wells (the number of repetitions); in animal experiments, n is the number of animals in each group (the number of samples).

Figure 5:
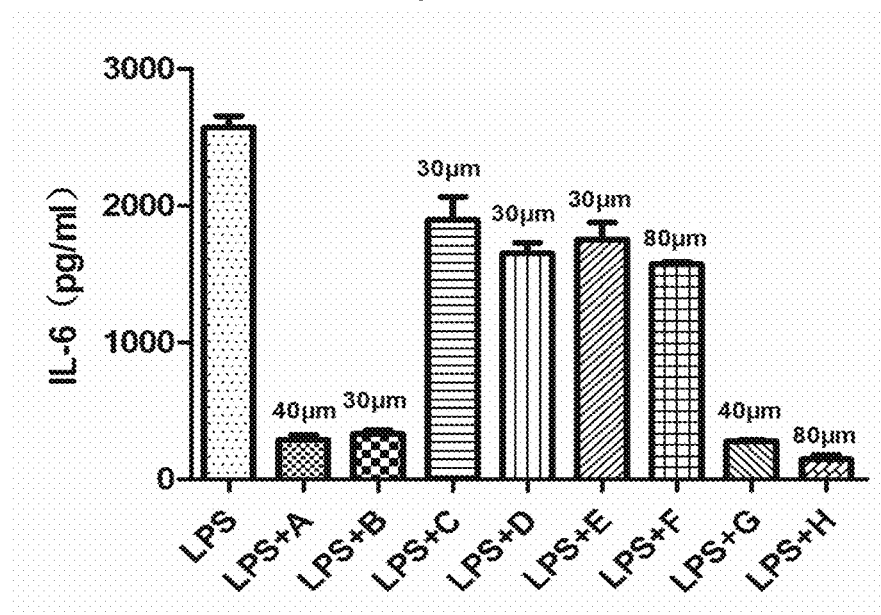
FIG. 5 is a diagram illustrating effects of compounds A to H on the level of IL-6 protein secreted by mouse macrophages RAW264.7 in Example 10 of the present application (n=3).
Figure 6:
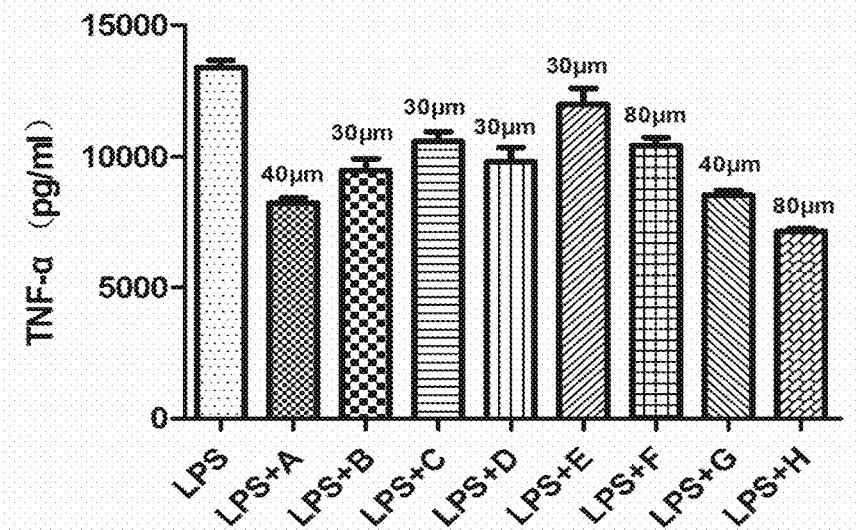
FIG. 6 is a diagram illustrating effects of compounds A to H on the level of TNF-α protein secreted by mouse macrophages RAW264.7 in Example 10 of the present application (n=3).
Figure 7:
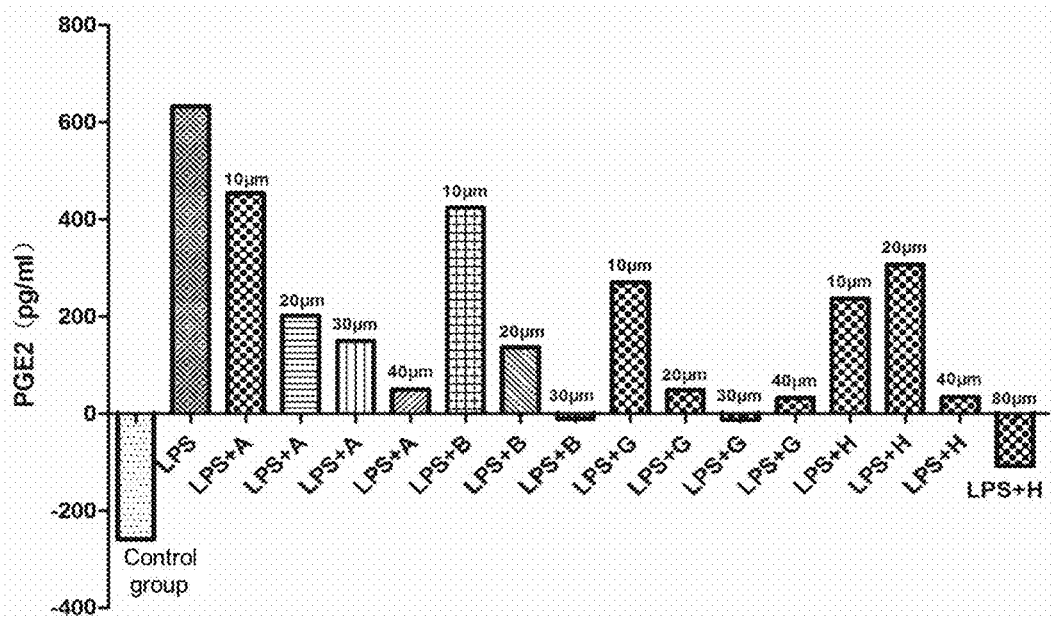
FIG. 7 is a diagram illustrating effects of compounds A, B, G, and H on the level of $PGE_2$ protein secreted by mouse macrophages RAW264.7 in Example 10 of the present application (n=3).

FIGS. 5, 6 and 7 show the effects of the myricanol derivatives on the anti-inflammatory activity of the mouse macrophages RAW 264.7 (n=3).

It can be seen from results in FIG. 5 that all the myricanol derivatives exhibit the effect of inhibiting IL-6 secreted by mouse macrophages RAW264.7 induced by LPS, and some compounds such as A, B, G, and H have very strong effects of inhibiting LPS-induced IL-6 secretion of RAW264.7 cells, which indicates that they may have an effect of inhibiting local inflammation of the serum or the intestinal tract of a patient with an inflammatory bowel disease.

It can be seen from results in FIG. 6 that some myricanol derivatives exhibit a significant effect of inhibiting TNF-α secreted by mouse macrophages RAW264.7 induced by LPS, which indicates that they may have an effect of inhibiting local inflammation of the serum or the intestinal tract of a patient with the inflammatory bowel disease.

It can be seen from results in FIG. 7 that some myricanol derivatives (A, B, G, and H) have a significant effect of inhibiting PGE$_2$ secreted by mouse macrophages RAW264.7 induced by LPS, which indicates that they may have an effect of inhibiting local inflammation of the serum or the intestinal tract of a patient with the inflammatory bowel disease.

Figure 8:
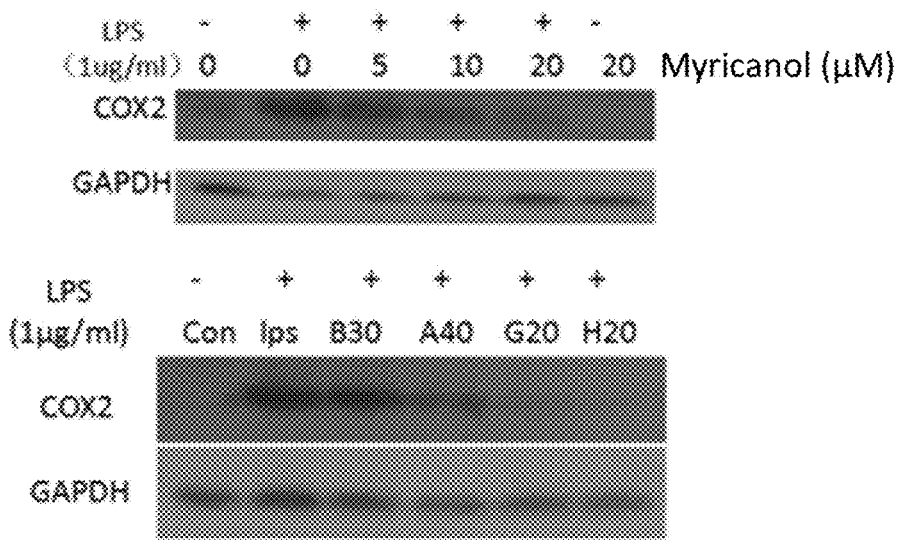
FIG. 8 is a diagram illustrating effects of compounds A, B, G, and H on COX2 protein expressed by mouse macrophages RAW264.7 in Example 10 of the present application.

It can be seen from results in FIG. 8 that myricanol and some derivatives thereof (A, B, G, and H) can inhibit the protein expression of IBD-related COX2, and derivatives G and H have better inhabitation effects than myricanol.

Figure 9:
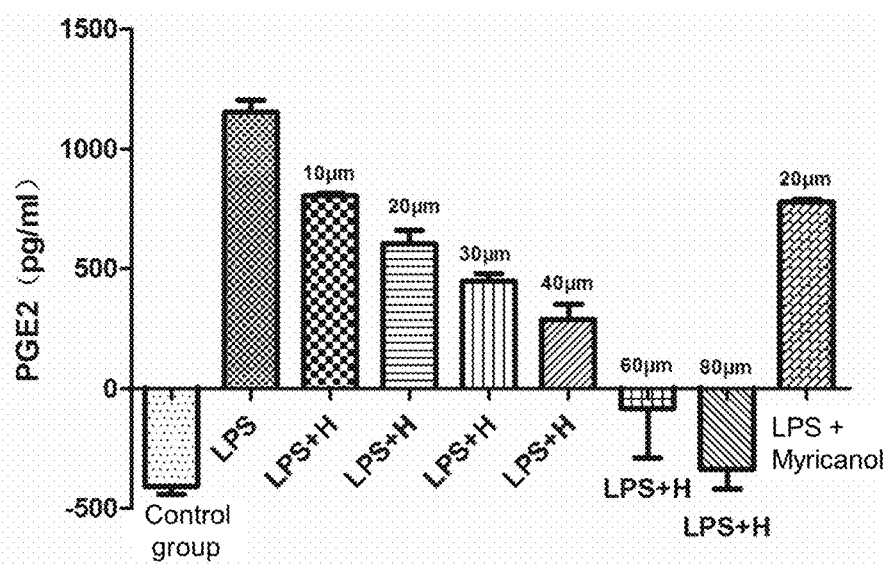
FIG. 9 is a diagram illustrating comparison of activity of compound H on the level of $PGE_2$ protein expressed by mouse macrophages RAW264.7 in Example 10 of the present application (n=3).

It can be seen from results in FIG. 9 that myricanol and its derivatives A, B, G, and H have a strong ability to inhibit the inflammatory factor $PGE_2$. It can be seen from FIG. 9 that the activity of derivative H for inhibiting $PGE_2$ is well dose-dependent, and has a better inhabitation effect than myricanol at a dose of 20 μM.

Inhabitation effects of myricanol and compound H on $PGE_2$ secreted by mouse macrophages RAW264.7 when induced by LPS are shown in Table 1.

TABLE 1

|  | $PGE_2$ (pg/mL) |
|---|---|
| Control group | −407.37 ± 57.67 |
| LPS | 1154.90 ± 84.20 |
| LPS ± H-10 μM | 804.30 ± 18.46 |
| LPS ± H-20 μM | 604.66 ± 97.52 |
| LPS ± H-30 μM | 448.16 ± 55.26 |
| LPS ± H-40 μM | 289.30 ± 109.41 |
| LPS ± H-60 μM | −82.01 ± 357.30 |
| LPS ± H-80 μM | −338.14 ± 138.40 |
| LPS ± myricanol-20 μM | 904.98 ± 18.02 |

Example 11

In this example, the in vivo pharmacodynamic activity of the myricanol derivative, compound H, on dextran sodium sulfate (DSS)-induced mouse in vivo models of IBD was tested.

Female SPF-grade C57BL/6 mice each with an age of 6 to 8 weeks were subjected to adaptive feeding for 3-7 days, and then fed with 5% aqueous solution of DSS in a free water-drinking manner (day0). The original aqueous solution of DSS was replaced with a fresh aqueous solution of DSS every 2 days. After the mice freely drank the aqueous solution of DSS for 7 days (day7), they were fed with fresh purified water. After 4 days of modeling, medicament was administered on the 5th day of modeling. Animals were administered via tail veins with 5 mg/kg, 2.5 mg/kg, and 1.25 mg/kg of the medicament for treatment. The animals were administered with the medicament for 4 continuous days, and then observed for 1 day. The experiments were terminated 24 h after the last administration.

Detection indexes: the weight of each group of animals was observed and recorded every day, and feces of each animal were collected to detect occult blood in the feces. If obvious blood in the feces cannot be determined, an occult blood detection kit was used for confirming the occult blood, and the result was recorded on an experimental record paper and photographed. When the experiments ended, animal serum was collected to detect the expression of IL-6 in the blood. At the same time, the fecal traits, occult blood, and weight change rate of each animal were scored, and the scores were added to give a DAI score for the animal. Colorectal tissue samples of the animals were collected for the subsequent pathological detection and detection of MPO in the tissue.

Figure 10:
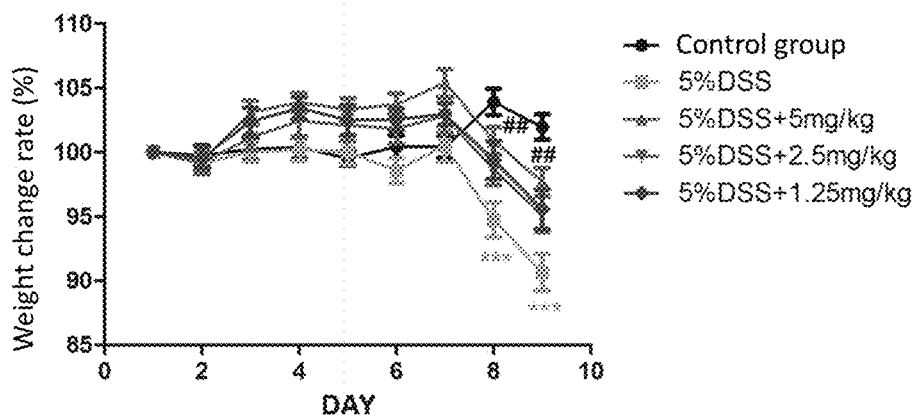
FIG. 10 is a diagram illustrating an effect of compound H on the weight change rate of an acute IBD model induced by 5% DSS in Example 11 of the present application (n=10) (blank group vs 5% DSS ***p<0.001; 5% DSS vs 5% DSS+5 mg/kg ##p<0.01).

It can be seen from results in FIG. 10 that the myricanol derivative H exhibits an effect of slowing the weight loss trend of the acute IBD mouse model induced by 5% DSS, which indicates that it can relieve the weight loss of a patient with an inflammatory bowel disease.

Figure 11:
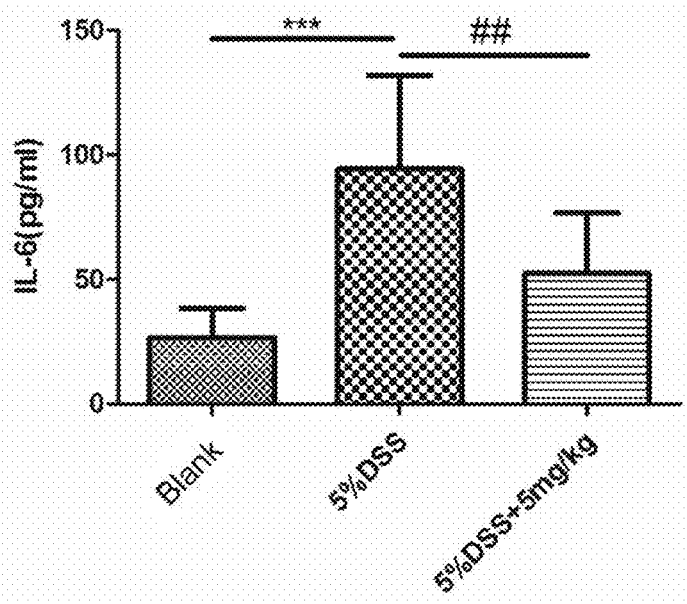
FIG. 11 is a diagram illustrating an effect of compound H on the level of IL-6 protein in serum of an acute IBD model induced by 5% DSS in Example 11 of the present application (n=10).

It can be seen from results in FIG. 11 that the myricanol derivative H exhibits a significant anti-inflammatory effect, which indicates that it can relieve the inflammatory response of a patient with an inflammatory bowel disease.

Figure 12:
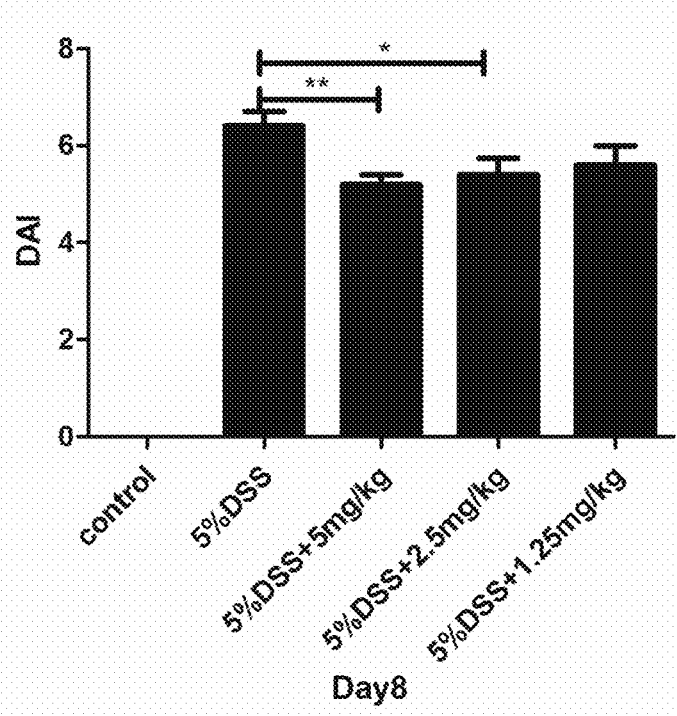
FIG. 12 is a diagram illustrating an effect of compound H on the DAI score of an acute IBD model induced by 5% DSS in Example 11 of the present application (n=10).

It can be seen from results in FIG. 12 that the myricanol derivative H exhibits a significant effect of reducing the DAI scores of mice, which indicates that it can improve the overall state of a patient with an inflammatory bowel disease and has an effect of relieving symptoms.

Figure 13:
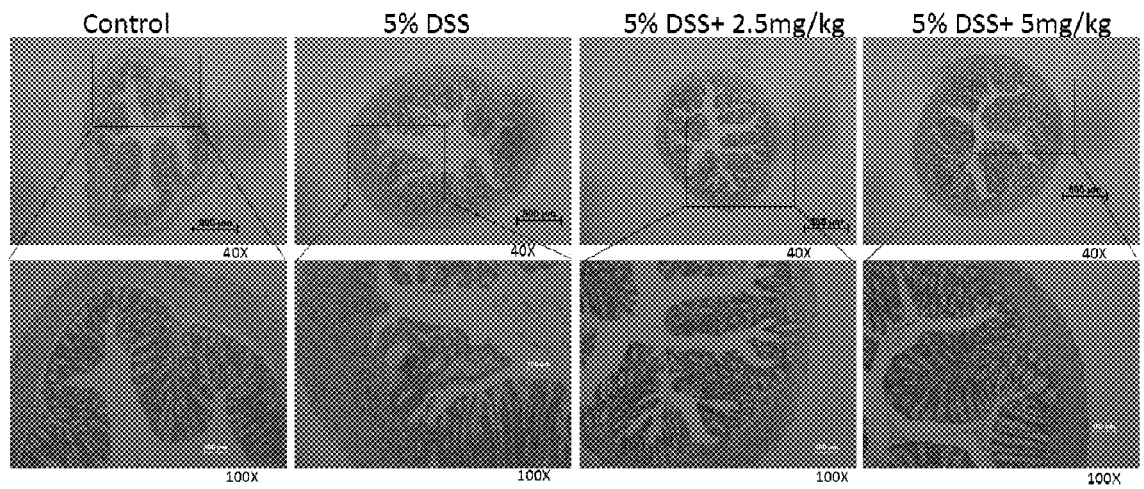
FIG. 13 is a diagram illustrating an effect of compound H on colorectal pathology of an acute IBD model induced by 5% DSS in Example 11 of the present application.

It can be seen from results in FIG. 13 that the myricanol derivative H exhibits a significant effect of repairing injuries of intestinal mucosa of C57BL/6 mice caused by 5% DSS, which indicates that it has an effect of improving the intestinal injuries of a patient with an inflammatory bowel disease.

Figure 14:
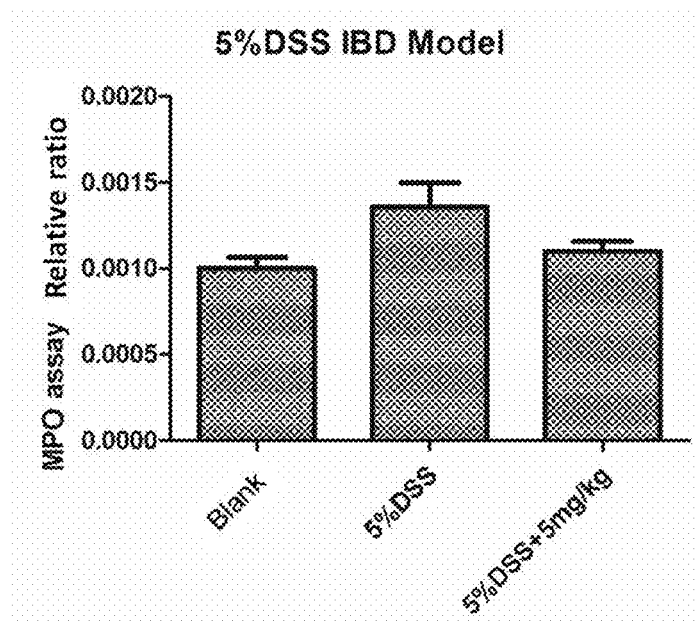
FIG. 14 is a diagram illustrating an effect of compound H on colorectal MPO of an acute IBD model induced by 5% DSS in Example 11 of the present application.

It can be seen from results in FIG. 14 that the myricanol derivative H has a certain effect of improving oxidative injuries of the colorectal tract of mice caused by 5% DSS.

Example 12

In this example, the in vivo pharmacodynamic activity of compound H on 2,4,6-trinitrobenzenesulfonic acid (TNBS)-induced rat in vivo models of IBD was tested.

Test method: female SPF-grade SD rats each with a weight of 180-200 g were subjected to adaptive feeding for 5-7 days, and then started to be modeled. At the time of modeling, the rats were anesthetized, a pre-labeled cat catheter was inserted through the anus into the colon for 8 cm, 250 μL of 2.5% (wt/vol) TNBS solution was slowly injected into the cavity of the colon, the rat was inverted for 1 min, and then the catheter was slowly removed from the intestine. The rat was hold with its head down towards for 1 min and then put back to a cage. Rats in a blank group were administered with the same volume of normal saline. On the second day of modeling, i.e., D1, the medicament was administered through intragastric administration for 6 continuous days.

Detection indexes: the weight of each group of animals was observed and recorded every day, and feces of each animal were collected at the beginning of experiments to detect occult blood in the feces. If obvious blood in the feces cannot be determined, an occult blood detection kit was used for confirming the occult blood, and the result was recorded on an experimental record paper and photographed. After the end of the experiments, the fecal traits, occult blood, and weight change rate of each animal were scored, and the scores were added to give a DAI score for each animal. Colorectal tissue samples of the animals were collected and a wet weight was weighted for the subsequent pathological detection.

Figure 15:
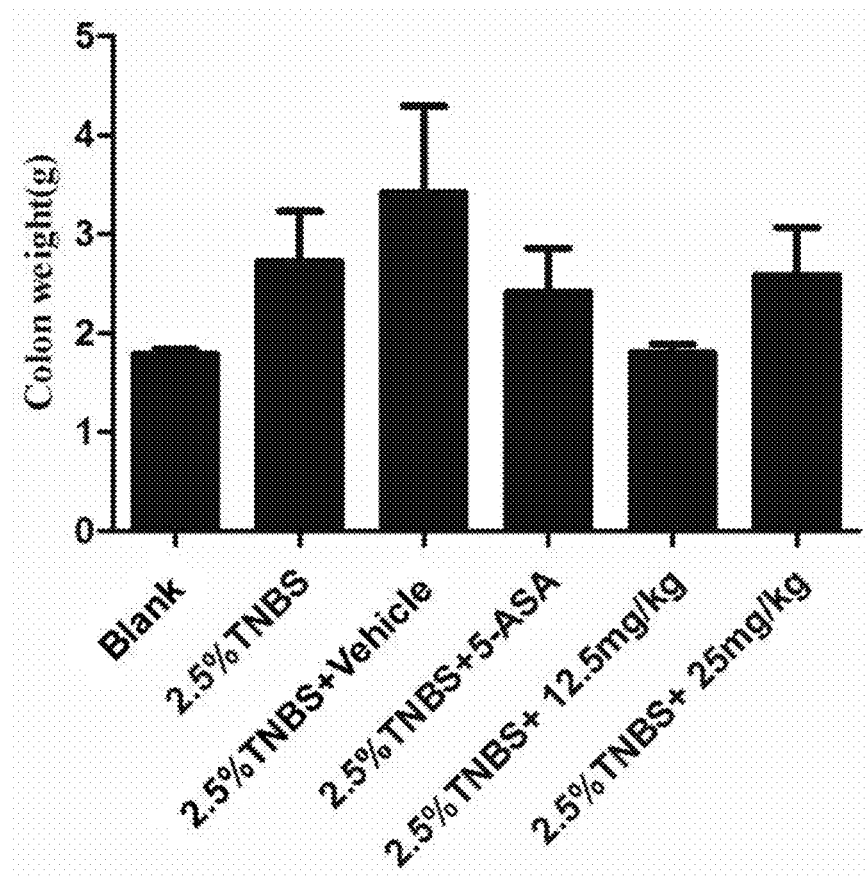
FIG. 15 is a schematic diagram of changes in wet weight of the colorectal of rats treated with compound H in Example 12 of the present application.

Experimental results show that after treated with 2.5% TNBS, the intestinal wet weight of the rat increases compared with the blank group and the treatment group with no statistical difference, but the group with the administration of H-12.5 mg/kg has the trend of reducing the edema of the rat (as shown in FIG. 15).

Figure 16:
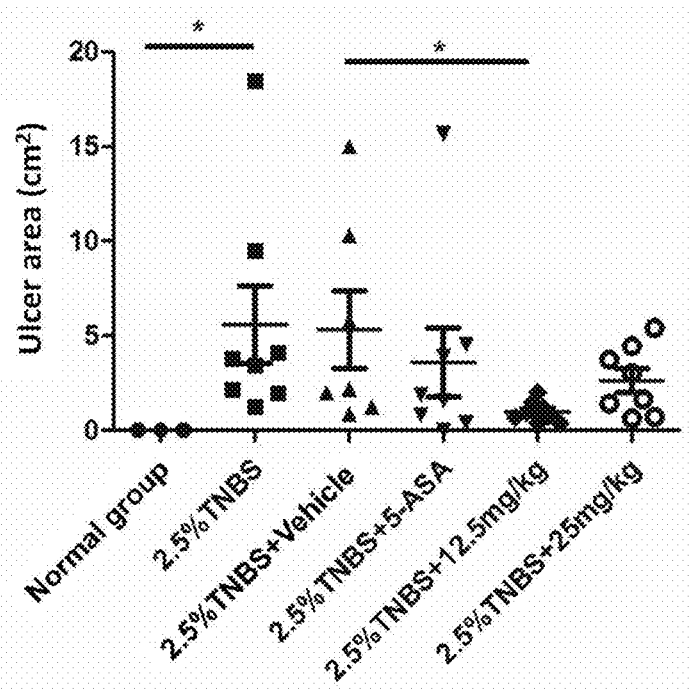
FIG. 16 is a schematic diagram of areas of colorectal ulcers of rats treated with compound H in Example 12 of the present application.

Experimental results: the oral administration of 12.5 mg/kg-H has an effect of significantly reducing the area of colorectal ulcers of the IBD model induced by 2.5% TNBS (as shown in FIG. 16) and has slightly better efficacy than 5-aminosalicylic acid (5-ASA) as for this index.

Experimental results: the oral administration of 12.5 mg/kg-H has an effect of significantly reducing the level of colorectal inflammation of the IBD model induced by 2.5%

Figure 17:
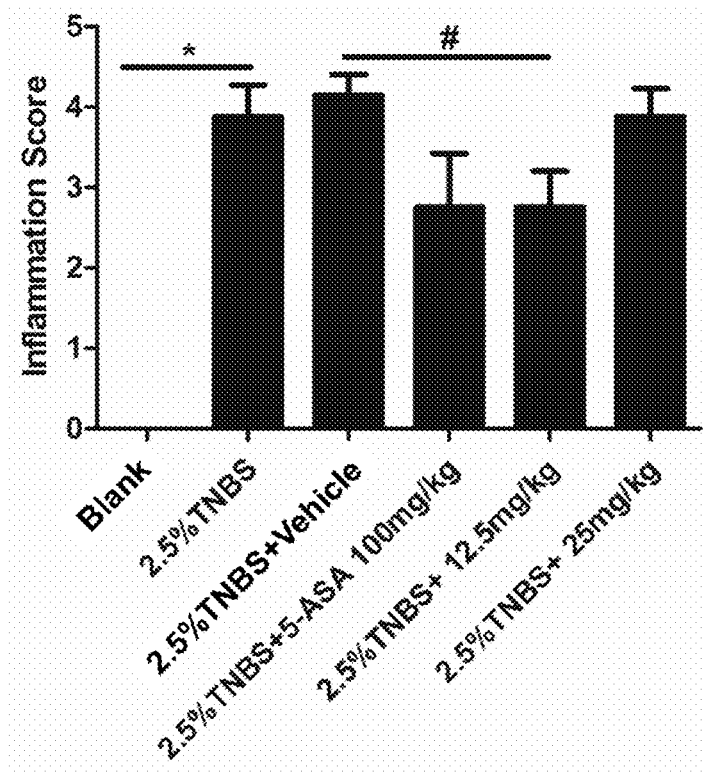
FIG. 17 is a schematic diagram of inflammation scores of colorectal pathological HE of rats treated with compound H in Example 12 of the present application ($p<0.05$ vs blank #$p<0.05$ vs 2.5% TNBS+vehicle).

TNBS and has the substantially same efficacy as 5-aminosalicylic acid (5-ASA) as for this index (as shown in FIG. 17).

Figure 18:
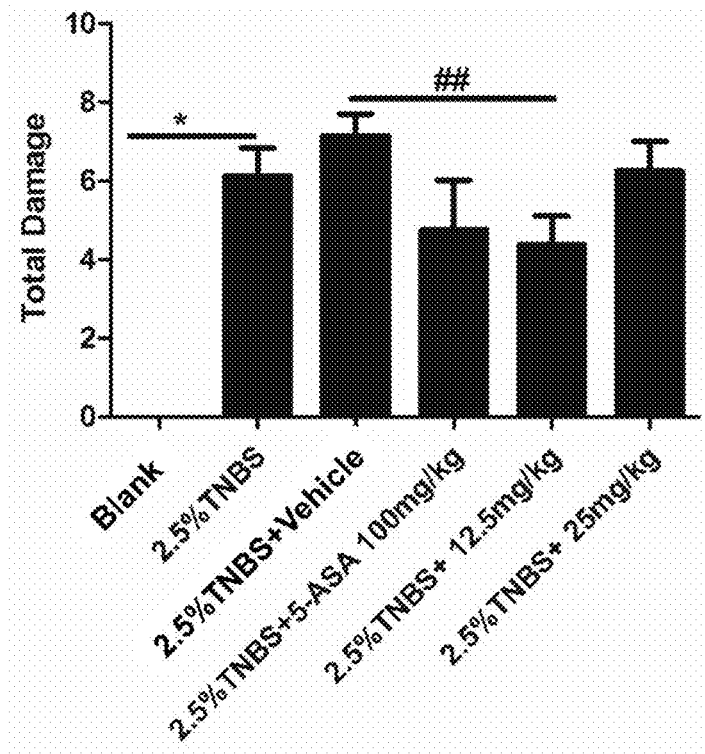
FIG. 18 is a schematic diagram of scores of total injuries of colorectal pathological HE of rats treated with compound H in Example 12 of the present application (*$p<0.05$ vs blank ##$p<0.01$ vs 2.5% TNBS+vehicle).

Experimental results: the oral administration of 12.5 mg/kg-H has an effect of significantly reducing the level of colorectal total injures of the IBD model induced by 2.5% TNBS and has the substantially same efficacy as 5-aminosalicylic acid (5-ASA) as for this index (as shown in FIG. 18).

Figure 19:
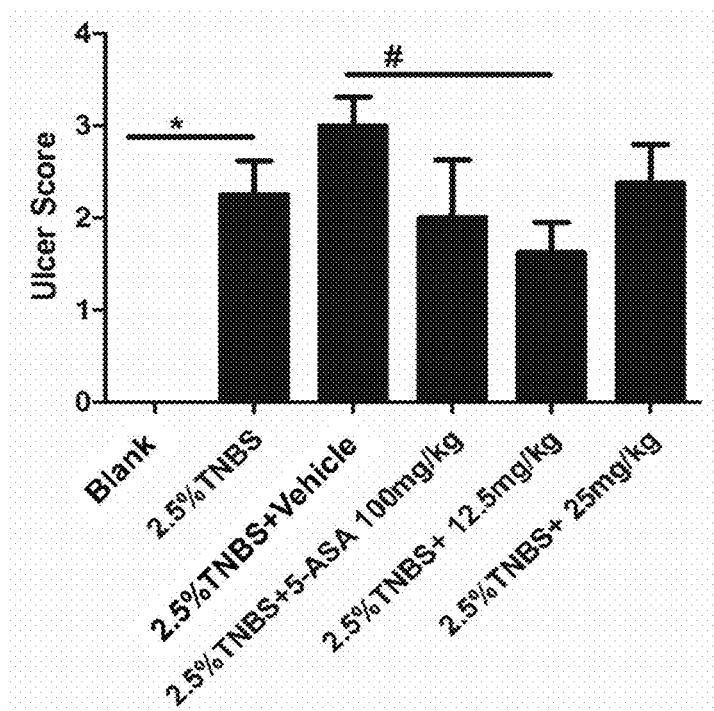
FIG. 19 is a schematic diagram of scores of ulcerative injuries of colorectal pathological HE of rats treated with compound H in Example 12 of the present application (*$p<0.05$ vs blank #$p<0.05$ vs 2.5% TNBS+vehicle).

Experimental results: the oral administration of 12.5 mg/kg-H has an effect of significantly reducing the injury score of colorectal ulcers of the IBD model induced by 2.5% TNBS and has slightly better efficacy than 5-aminosalicylic acid (5-ASA) as for this index (as shown in FIG. 19).

Figure 20:
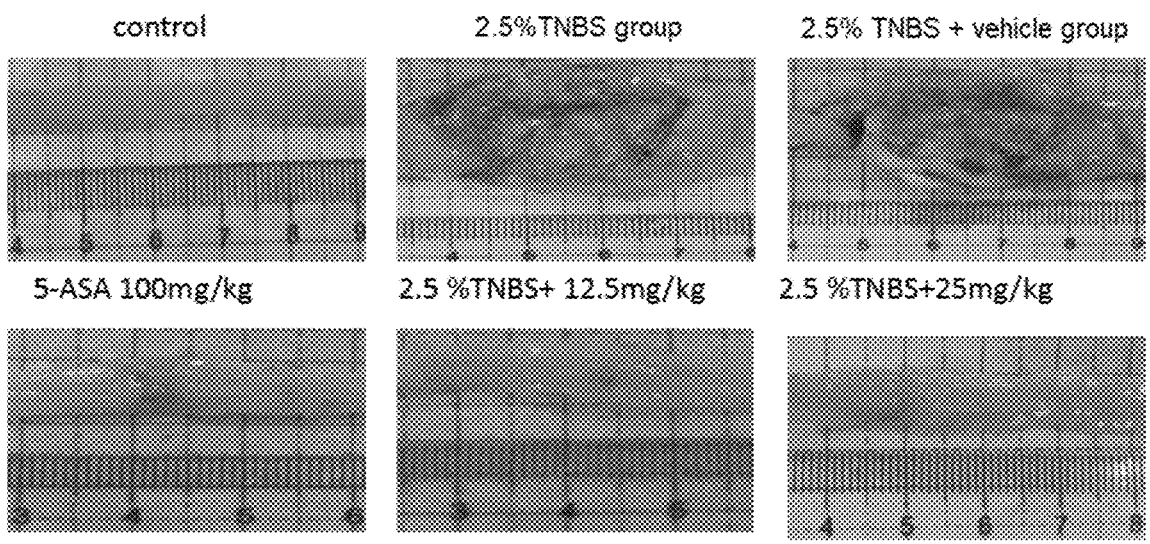
FIG. 20 is a schematic diagram of anatomical colorectal injuries of rats treated with compound H in Example 12 of the present application.
Figure 21:
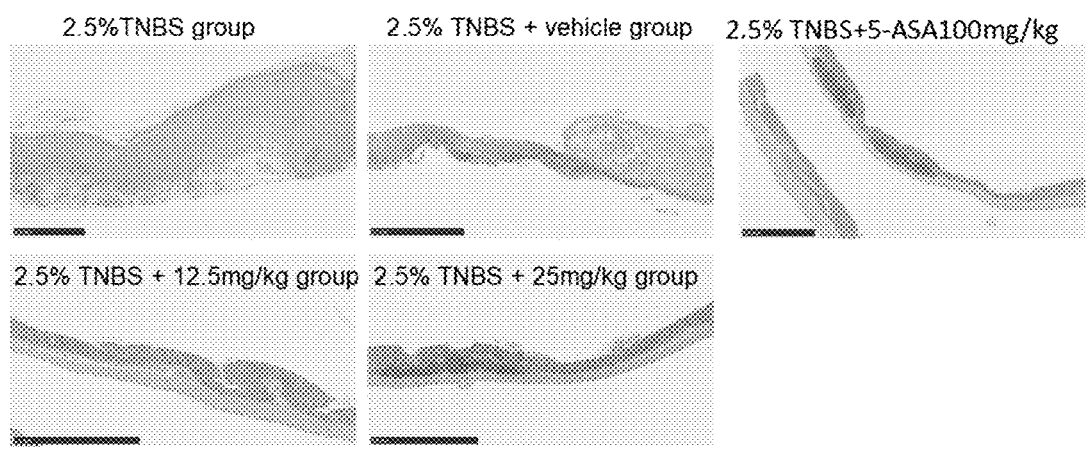
FIG. 21 is a schematic diagram of colorectal pathological HE of rats treated with compound H in Example 12 of the present application.

Experimental results: the oral administration of 12.5 mg/kg-H and the oral administration of 25 mg/kg-H has an effect of reducing injuries of colorectal ulcers of the IBD model induced by 2.5% TNBS (as shown in FIGS. 20 and 21).

Pathological observation results show that the oral administration of 12.5 mg/kg-H has an effect of significantly improving the score of colorectal inflammation of the IBD model rat induced by 2.5% TNBS (as shown in FIG. 17), significantly reducing the degree of overall colorectal injuries of the IBD model rat induced by 2.5% TNBS (as shown in FIG. 18), and significantly reducing the severity of injuries of the IBD model rat induced by 2.5% TNBS (as shown in FIGS. 19, 20 and 21).

The above experimental results indicate that the myricanol derivative, compound H, has a good anti-inflammatory bowel disease effect.

Example 13

In this example, acute toxicity of compounds A, B, G, and H was tested by specific steps below.

Trial method: 30 SD rats, half male and half female, were used. The average weight was 160-200 g for female rats and 180-220 g for male rats when grouped. An individual weight should be within ±20% of the average weight. Before the test, animals needed to accommodate to the environment for at least 5 days, and healthy rats (female rats should be not pregnant) were selected as test animals. Matter detected during the accommodation period mainly was: whether the rats were consistent with quality indexes required in the order; detection of general conditions; and whether the weight was within the weight range required by the test. Unqualified abnormal animals were excluded from the test. A single dosage was orally administered to rats at a low, medium, or high dose. The doses were adjusted to be 100 mg/kg, 300 mg/kg, and 1000 mg/kg, respectively according to blank preparation pre-experiments. A control group was set with the oral administration of the same volume of solvent.

Observation method: (1) Observation of general conditions: rats were observed for appearance signs, administration sites (whether there was bleeding, redness, bruising, induration, purulence, ulceration), hair coats, general behaviors, mental status, gland secretion, skin and mucous membrane colors, respiratory status, feces traits, genitalia, death, etc. and other toxicity symptoms. The rats were observed about 0-2 h and 4-6 h after each administration. If a toxicity symptom occurs, the rats may be observed more times. (2) Gross anatomical observation: on the 14th day of the test, all surviving rats in each group were dissected and observed, and for administration sites and gross dissection, abnormal organs and tissues which were observed and found to be potentially related to test samples were photographed and recorded. (3) Disposal of dying animals: status of rats and observation time were recorded, and their weights were measured. (4) Disposal of dead animals: the time of death or when a rat was found dead were recorded. The rat was measured for weight before quickly dissected for gross observation and speculated for a cause of death. Doses and results of the acute toxicity of compounds A, B, G, and H are shown in Table 2.

TABLE 2

| No. | Group | Dose | Administration | Test Endpoint |
|---|---|---|---|---|
| 1 | A | 100 mg/kg | Intragastric administration | No obvious toxic side effects |
|   |   | 300 mg/kg | Intragastric administration | No obvious toxic side effects |
|   |   | 1000 mg/kg | Intragastric administration | No obvious toxic side effects |
| 2 | B | 100 mg/kg | Intragastric administration | No obvious toxic side effects |
|   |   | 300 mg/kg | Intragastric administration | No obvious toxic side effects |
|   |   | 1000 mg/kg | Intragastric administration | No obvious toxic side effects |
| 3 | G | 100 mg/kg | Intragastric administration | No obvious toxic side effects |
|   |   | 300 mg/kg | Intragastric administration | No obvious toxic side effects |
|   |   | 1000 mg/kg | Intragastric administration | No obvious toxic side effects |
| 4 | H | 100 mg/kg | Intragastric administration | No obvious toxic side effects |
|   |   | 300 mg/kg | Intragastric administration | No obvious toxic side effects |
|   |   | 1000 mg/kg | Intragastric administration | No obvious toxic side effects |
|   |   | 1500 mg/kg | Intragastric administration | No obvious toxic side effects |

Experimental results: the SD rats exhibit no obvious toxic side effects and no obvious weight loss and diet decrease trends after a single dosage of intragastric administration of the above compounds. It indicates that the tolerance to the acute toxicity of a single dosage of the myricanol derivatives is MTD>1000 mg/kg, and for H, MTD>1500 mg/kg.

In can be seen in conjunction with the above-mentioned examples of the present application that the medicament having an anti-inflammatory bowel disease effect in the present application is synthesized from raw materials derived from natural products which are green and environmentally friendly through a simple synthesis process easy to control; and from the perspective of pharmacodynamic experiments, such compounds can be widely used as medicaments for treating the inflammatory bowel disease (IBD) without obvious side effects and have a broad application prospect.

The applicant has stated that although the medicament having an anti-inflammatory bowel disease effect, the preparation method thereof, and the application thereof in the present application are described through the above-mentioned examples, the present application is not limited to the above-mentioned processes and steps, which means that the implementation of the present application does not necessarily depend on the above-mentioned processes and steps. It should be apparent to those skilled in the art that any improvements made to the present application, equivalent replacements of raw materials selected in the present application and additions of adjuvant ingredients thereof, and selections of specific methods, etc., all fall within the protection scope and the disclosed scope of the present application.

What is claimed is:

1. A method for treating an inflammatory bowel disease, comprising administering to a patient a medicament having an anti-inflammatory bowel disease effect, wherein the medicament comprises a compound with the structure represented by Formula I or Formula II

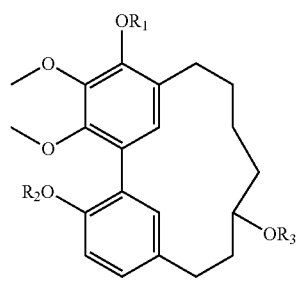

Formula I

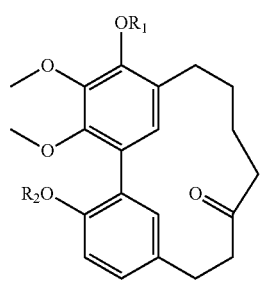

Formula II wherein $R_1$ and $R_2$ are each independently selected from any one of hydrogen, ethyl, n-propyl, n-butyl, isopropyl, allyl, isobutyl, t-butyl, benzyl, acetyl, a sulfonic acid group, a phosphoric acid group, a benzoic acid group, a benzamido group, a benzoylcyclopropylamino group, a benzenesulfonic acid group, a picolinamido group, a picolinoylcyclopropylamino group, a pyrimidinecarboxamido group, or a cyclopropylpyrimidinecarboxamido group;

$R_3$ is selected from any one of hydrogen, acetyl, a sulfonic acid group, or a phosphoric acid group; and in Formula I, $R_1$, $R_2$, and $R_3$ are not hydrogen at the same time; $R_1$, $R_2$, and $R_3$ are not acetyl at the same time; and $R_1$ and $R_2$ are not benzyl at the same time; and in Formula II, $R_1$ and $R_2$ are not hydrogen or benzyl at the same time, or a hydrate or pharmaceutically-acceptable salt thereof.

2. The method of claim 1, wherein the compound is in the form of a pharmaceutically acceptable salt.

3. The method of claim 2, wherein the pharmaceutically acceptable salt is a metal salt of a compound represented by Formula I or a metal salt of a compound represented by Formula II.

4. The method of claim 3, wherein the metal salt is a lithium salt, a sodium salt, a potassium salt, a magnesium salt, or a calcium salt.

5. The method of claim 1, wherein the medicament has any one of following compound structures A to J:

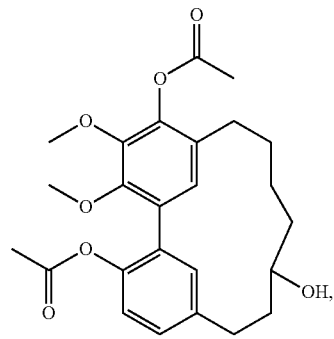

A

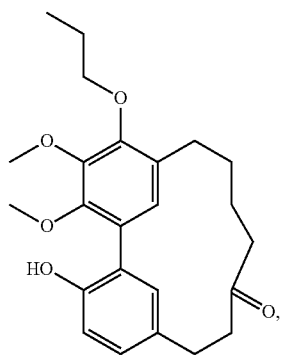

B

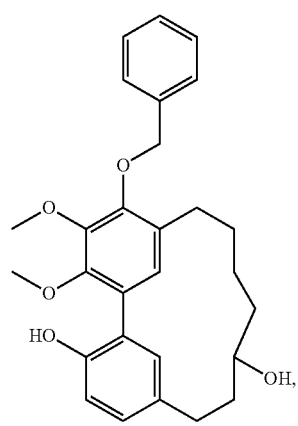

C

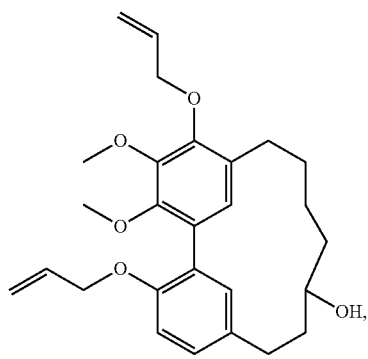

D

6. The method of claim 1, wherein the medicament further comprises an adjuvant.

7. The method of claim 6, wherein the adjuvant comprises any one or a combination of at least two of an excipient, a diluent, a carrier, a flavoring agent, a binder, or a filler.

8. The method of claim 1, wherein the medicament is in the form of an oral preparation, an external preparation, or a parenteral preparation.

9. A method for treating an inflammatory bowel disease, comprising administering to a patient a pharmaceutical composition comprising the medicament of claim 1 and a pharmaceutically-acceptable carrier or excipient.

* * * * *